(12) United States Patent
Luciano, Jr. et al.

(10) Patent No.: US 9,238,518 B2
(45) Date of Patent: Jan. 19, 2016

(54) INSPECTION SYSTEM AND METHOD WITH A CONTROL PROCESS THAT INSPECTS DIFFERENT MEDICATIONS

(75) Inventors: Robert A. Luciano, Jr., Reno, NV (US); Warren White, Reno, NV (US)

(73) Assignee: EDGE MEDICAL PROPERTIES, LLC, Reno, NV (US)

( * ) Notice: Subject to any disclaimer, the term of this patent is extended or adjusted under 35 U.S.C. 154(b) by 745 days.

(21) Appl. No.: 13/473,267

(22) Filed: May 16, 2012

(65) Prior Publication Data

US 2012/0290129 A1 Nov. 15, 2012

Related U.S. Application Data

(63) Continuation-in-part of application No. 13/357,483, filed on Jan. 24, 2012, and a continuation-in-part of application No. 11/241,783, filed on Sep. 30, 2005, now Pat. No. 8,123,036, application No. 13/473,267, (Continued)

(51) Int. Cl.
*B65B 57/10* (2006.01)
*B65B 5/10* (2006.01)
(Continued)

(52) U.S. Cl.
CPC .............. *B65B 57/10* (2013.01); *B65B 5/103* (2013.01); *B65B 35/54* (2013.01); *B65D 75/42* (2013.01); *G01N 21/9508* (2013.01); *G07F 17/0092* (2013.01); *B65B 9/06* (2013.01)

(58) Field of Classification Search
CPC ........ A61J 7/0084; B65B 57/10; B65B 5/103; B65B 35/54; G01N 21/9508; G07F 17/0092; G06F 19/3462; G07C 3/146

USPC ......... 53/396, 473, 474, 52, 53, 54, 502, 154, 53/235, 237; 382/141, 143; 700/244; 702/81, 82, 84
See application file for complete search history.

(56) References Cited

U.S. PATENT DOCUMENTS 2,294,220 A 8/1942 Albertson
3,126,129 A 3/1964 Weinberg
(Continued)

FOREIGN PATENT DOCUMENTS

DE 3502647 A1 7/1986
WO WO 96/13790 A1 5/1996
(Continued)

*Primary Examiner* — Stephen F Gerrity
(74) *Attorney, Agent, or Firm* — Kerr IP Group LLC; Michael A. Kerr

(57) ABSTRACT

An inspection system and method that inspects at least two different medications is described. The automated filling station houses at least two different medications. The automated inspection station receives the medications associated with one of the packages. The measurement device associated with the automated inspection station is configured to examine the different medications and generate a measured medication value for the different medications. The measured medication value is received by the inspection control process module. Additionally, the expected medication value is received by the inspection control process module. The inspection result state is then selected by the inspection control process module. The inspection control module compares the expected medication value to the measured medication value. The inspection result state includes a positive inspection result state, a negative inspection result state, and an inconclusive inspection result state.

30 Claims, 13 Drawing Sheets

Related U.S. Application Data which is a continuation-in-part of application No. 13/312,907, filed on Dec. 6, 2011, now Pat. No. 9,015,058, and a continuation-in-part of application No. 13/312,888, filed on Dec. 6, 2011, now Pat. No. 8,972,288, application No. 13/473,267, which is a continuation-in-part of application No. 12/945,709, filed on Nov. 12, 2010, now Pat. No. 9,141,764, and a continuation-in-part of application No. 12/896,284, filed on Oct. 1, 2010, application No. 13/473,267, which is a continuation-in-part of application No. 12/896,275, filed on Oct. 1, 2010, now Pat. No. 8,914,298, application No. 13/473,267, which is a continuation-in-part of application No. 12/896,134, filed on Oct. 1, 2010, now Pat. No. 8,712,582, application No. 13/473,267, which is a continuation-in-part of application No. 12/891,042, filed on Sep. 27, 2010, application No. 13/473,267, which is a continuation-in-part of application No. 12/891,029, filed on Sep. 27, 2010, application No. 13/473,267, which is a continuation-in-part of application No. 12/696,884, filed on Jan. 29, 2010, now Pat. No. 8,931,241, and a continuation-in-part of application No. 12/684,640, filed on Jan. 8, 2010, and a continuation-in-part of application No. 12/684,664, filed on Jan. 8, 2010, and a continuation-in-part of application No. 12/684,060, filed on Jan. 7, 2010, now Pat. No. 8,789,700, which is a continuation-in-part of application No. 11/796,123, filed on Apr. 25, 2007, now Pat. No. 7,690,173, application No. 13/473,267, which is a continuation-in-part of application No. 12/631,586, filed on Dec. 4, 2009, now Pat. No. 8,777,012, and a continuation-in-part of application No. 12/424,483, filed on Apr. 15, 2009, and a continuation-in-part of application No. 12/424,475, filed on Apr. 15, 2009, now Pat. No. 8,146,747, application No. 13/473,267, which is a continuation-in-part of application No. 12/418,436, filed on Apr. 3, 2009, now abandoned, and a continuation-in-part of application No. 11/796,125, filed on Apr. 25, 2007, and a continuation-in-part of application No. 12/418,422, filed on Apr. 3, 2009, now abandoned, application No. 13/473,267, which is a continuation-in-part of application No. 11/923,321, filed on Oct. 24, 2007, now Pat. No. 8,266,878, application No. 13/473,267, which is a continuation-in-part of application No. 11/796,124, filed on Apr. 25, 2007, now Pat. No. 8,074,426.

(60) Provisional application No. 61/486,427, filed on May 16, 2011, provisional application No. 61/486,436, filed on May 16, 2011, provisional application No. 60/615,267, filed on Oct. 1, 2004, provisional application No. 61/420,151, filed on Dec. 6, 2010, provisional application No. 61/498,489, filed on Jun. 17, 2011, provisional application No. 61/420,140, filed on Dec. 6, 2010, provisional application No. 61/248,471, filed on Oct. 4, 2009, provisional application No. 61/245,912, filed on Sep. 25, 2009, provisional application No. 61/245,899, filed on Sep. 25, 2009, provisional application No. 60/854,341, filed on Oct. 24, 2006, provisional application No. 61/045,160, filed on Apr. 15, 2008, provisional application No. 61/045,166, filed on Apr. 15, 2008, provisional application No. 61/045,171, filed on Apr. 15, 2008, provisional application No. 61/042,262, filed on Apr. 3, 2008, provisional application No. 61/042,263, filed on Apr. 3, 2008, provisional application No. 60/795,370, filed on Apr. 26, 2006, provisional application No. 60/795,446, filed on Apr. 26, 2006, provisional application No. 60/795,413, filed on Apr. 26, 2006.

(51) Int. Cl.
*B65B 35/54* (2006.01)
*B65D 75/42* (2006.01)
*G01N 21/95* (2006.01)
*G07F 17/00* (2006.01)
*B65B 9/06* (2012.01)

(56) References Cited

U.S. PATENT DOCUMENTS

| | | | |
|---|---|---|---|
| 3,254,828 A | 6/1966 | Lerner | |
| 3,308,962 A | 3/1967 | Bryant | |
| 3,409,721 A | 11/1968 | Applezweig | |
| 3,410,450 A | 11/1968 | Fortenberry | |
| 3,432,951 A | 3/1969 | Cherrin | |
| 3,450,306 A | 6/1969 | Gill | |
| 3,497,982 A | 3/1970 | Schultz | |
| 3,503,493 A | 3/1970 | Nagy | |
| 3,703,955 A | 11/1972 | Inacker | |
| 3,780,856 A | 12/1973 | Braverman | |
| 3,921,804 A | 11/1975 | Tester | |
| 3,933,245 A | 1/1976 | Mullen | |
| 4,039,080 A | 8/1977 | Cappuccilli | |
| 4,062,445 A | 12/1977 | Moe | |
| 4,274,550 A | 6/1981 | Feldstein | |
| 4,318,477 A | 3/1982 | Kerpe | |
| 4,416,375 A | 11/1983 | Braverman et al. | |
| 4,512,476 A | 4/1985 | Herrington, Jr. | |
| 4,535,890 A | 8/1985 | Artusi | |
| 4,546,901 A | 10/1985 | Buttarazzi | |
| 4,553,670 A | 11/1985 | Collens | |
| 4,655,026 A | 4/1987 | Wigoda | |
| 4,693,371 A | 9/1987 | Malpass | |
| 4,749,085 A | 6/1988 | Denney | |
| 4,799,590 A | 1/1989 | Furman | |
| 4,805,800 A | 2/1989 | Nocek et al. | |
| 4,811,764 A * | 3/1989 | McLaughlin | 141/98 |
| 4,832,229 A | 5/1989 | Hackmann et al. | |
| 4,850,489 A | 7/1989 | Weithmann et al. | |
| 4,860,899 A | 8/1989 | McKee | |
| 4,867,315 A | 9/1989 | Baldwin | |
| 4,872,559 A | 10/1989 | Schoon | |
| 4,887,790 A | 12/1989 | Wilkinson et al. | |
| 4,918,604 A | 4/1990 | Baum | |
| 4,953,745 A | 9/1990 | Rowlett, Jr. | |
| 4,972,657 A | 11/1990 | McKee | |
| 5,014,851 A | 5/1991 | Wick | |
| 5,085,510 A * | 2/1992 | Mitchell | 356/237.1 |
| 5,186,345 A | 2/1993 | Ching An | |
| 5,195,123 A | 3/1993 | Clement | |
| 5,199,636 A | 4/1993 | Young | |
| 5,310,057 A | 5/1994 | Caldwell et al. | |
| 5,366,087 A | 11/1994 | Bane | |
| 5,390,796 A | 2/1995 | Kerfoot, Jr. | |
| 5,422,831 A * | 6/1995 | Misra et al. | 702/81 |
| 5,457,895 A | 10/1995 | Thompson et al. | |
| 5,505,371 A | 4/1996 | O'Neill | |
| 5,522,512 A | 6/1996 | Archer et al. | |
| 5,558,229 A | 9/1996 | Halbich | |
| 5,577,612 A | 11/1996 | Chesson et al. | |
| 5,597,995 A | 1/1997 | Williams et al. | |
| 5,642,906 A | 7/1997 | Foote et al. | |
| 5,671,592 A | 9/1997 | Yayama et al. | |
| 5,737,539 A | 4/1998 | Edelson et al. | |
| 5,746,323 A * | 5/1998 | Dragotta | 209/539 |
| 5,788,079 A | 8/1998 | Bouthiette | |
| 5,788,974 A | 8/1998 | D'Amico et al. | |
| D400,412 S | 11/1998 | Gold | |
| 5,837,466 A | 11/1998 | Lane et al. | |
| 5,878,887 A | 3/1999 | Parker et al. | |
| 5,883,370 A | 3/1999 | Walker et al. | |

(56) References Cited

U.S. PATENT DOCUMENTS

| | | | |
|---|---|---|---|
| 5,899,333 A | 5/1999 | Williams et al. | |
| 5,921,398 A | 7/1999 | Carroll | |
| 5,963,453 A | 10/1999 | East | |
| 5,995,938 A | 11/1999 | Whaley | |
| 6,012,582 A | 1/2000 | Haygeman et al. | |
| 6,021,392 A | 2/2000 | Lester et al. | |
| 6,021,623 A | 2/2000 | Bouthiette | |
| 6,023,916 A | 2/2000 | Bouthiette | |
| 6,066,374 A | 5/2000 | Healy et al. | |
| 6,068,156 A | 5/2000 | Liff et al. | |
| 6,077,530 A | 6/2000 | Weinstein et al. | |
| 6,115,996 A | 9/2000 | Yuyama et al. | |
| 6,129,211 A | 10/2000 | Prakken et al. | |
| 6,155,423 A | 12/2000 | Katzner et al. | |
| 6,155,485 A | 12/2000 | Coughlin et al. | |
| 6,170,230 B1 | 1/2001 | Chudy et al. | |
| 6,181,979 B1 * | 1/2001 | Murakami | 700/216 |
| 6,202,923 B1 | 3/2001 | Boyer et al. | |
| 6,227,371 B1 | 5/2001 | Song | |
| 6,273,260 B1 | 8/2001 | ColDepietro et al. | |
| 6,293,403 B1 | 9/2001 | Holmberg | |
| 6,308,494 B1 | 10/2001 | Yuyama et al. | |
| 6,317,648 B1 | 11/2001 | Sleep et al. | |
| 6,318,630 B1 | 11/2001 | Coughlin et al. | |
| 6,324,253 B1 | 11/2001 | Yuyama et al. | |
| 6,330,351 B1 * | 12/2001 | Yasunaga | 382/141 |
| 6,343,695 B1 | 2/2002 | Petrick et al. | |
| D455,057 S | 4/2002 | Medhurst | |
| 6,371,297 B1 | 4/2002 | Cha | |
| 6,375,956 B1 | 4/2002 | Hermelin et al. | |
| 6,378,572 B1 * | 4/2002 | Neubauer et al. | 141/94 |
| 6,401,919 B1 | 6/2002 | Griffis et al. | |
| 6,449,921 B1 * | 9/2002 | Kim | 53/154 |
| 6,449,927 B2 | 9/2002 | Hebron et al. | |
| 6,460,693 B1 | 10/2002 | Harrold | |
| 6,505,461 B1 | 1/2003 | Yasunaga | |
| 6,523,694 B2 | 2/2003 | Lux, Jr. et al. | |
| 6,527,138 B2 | 3/2003 | Pawlo et al. | |
| 6,535,637 B1 | 3/2003 | Wootton et al. | |
| 6,564,945 B1 | 5/2003 | Weinstein et al. | |
| 6,581,798 B2 | 6/2003 | Liff et al. | |
| 6,594,928 B1 | 7/2003 | Clawson et al. | |
| 6,611,733 B1 | 8/2003 | De La Huerga | |
| 6,662,081 B1 | 12/2003 | Jacober et al. | |
| 6,681,935 B1 | 1/2004 | Lewis | |
| 6,690,998 B1 * | 2/2004 | Yuyama | 700/242 |
| 6,711,460 B1 | 3/2004 | Reese | |
| 6,735,497 B2 | 5/2004 | Wallace et al. | |
| 6,738,723 B2 | 5/2004 | Hamilton | |
| 6,757,898 B1 | 6/2004 | Ilsen et al. | |
| 6,771,369 B2 | 8/2004 | Rzasa | |
| 6,808,461 B2 | 10/2004 | Harris et al. | |
| 6,839,403 B1 | 1/2005 | Kotowski et al. | |
| 6,892,512 B2 | 5/2005 | Rice et al. | |
| 6,925,774 B2 | 8/2005 | Peterson | |
| 6,962,266 B2 | 11/2005 | Morgan et al. | |
| 6,981,592 B2 | 1/2006 | Siegel | |
| 6,990,998 B1 | 1/2006 | Amellal et al. | |
| 7,006,893 B2 | 2/2006 | Hart et al. | |
| 7,010,899 B2 | 3/2006 | McErlean et al. | |
| 7,017,513 B2 | 3/2006 | Giewercer | |
| 7,017,748 B2 | 3/2006 | Weinstein | |
| 7,028,723 B1 | 4/2006 | Alouani et al. | |
| 7,055,294 B1 | 6/2006 | Lewis | |
| 7,089,131 B2 * | 8/2006 | Thouin et al. | 702/82 |
| 7,111,780 B2 | 9/2006 | Broussard et al. | |
| 7,185,476 B1 | 3/2007 | Siegel et al. | |
| 7,225,597 B1 | 6/2007 | Knoth | |
| 7,317,525 B2 | 1/2008 | Rzasa et al. | |
| 7,398,279 B2 | 7/2008 | Muno et al. | |
| 7,426,814 B2 | 9/2008 | Knoth | |
| 7,509,787 B2 | 3/2009 | Ballestrazzi et al. | |
| 7,668,730 B2 | 2/2010 | Reardan et al. | |
| 7,747,345 B2 * | 6/2010 | Ohmura et al. | 700/231 |
| 7,828,148 B2 | 11/2010 | Gibson | |
| 8,055,512 B1 | 11/2011 | Pankow et al. | |
| 8,074,426 B2 * | 12/2011 | Luciano, Jr. et al. | 53/411 |
| 8,122,849 B2 | 2/2012 | Clarke et al. | |
| 8,123,036 B2 | 2/2012 | Luciano et al. | |
| 8,146,747 B2 | 4/2012 | Luciano et al. | |
| 8,196,774 B1 | 6/2012 | Clarke et al. | |
| 8,266,878 B2 | 9/2012 | Luciano et al. | |
| 8,556,077 B1 | 10/2013 | Hanley | |
| 8,712,582 B1 | 4/2014 | Luciano et al. | |
| 8,713,897 B2 | 5/2014 | Luciano et al. | |
| 8,752,704 B2 | 6/2014 | Leon Alonso et al. | |
| 8,777,012 B2 | 7/2014 | Luciano et al. | |
| 8,789,700 B2 | 7/2014 | Luciano et al. | |
| 8,914,298 B1 | 12/2014 | Luciano | |
| 8,931,241 B2 | 1/2015 | Luciano et al. | |
| 8,972,288 B2 | 3/2015 | Luciano, Jr. | |
| 2001/0041968 A1 | 11/2001 | Hamilton | |
| 2002/0029223 A1 | 3/2002 | Rice et al. | |
| 2002/0042725 A1 | 4/2002 | Mayaud | |
| 2002/0047019 A1 | 4/2002 | Devers | |
| 2002/0066691 A1 | 6/2002 | Varon | |
| 2002/0104778 A1 | 8/2002 | Lux et al. | |
| 2002/0117405 A1 | 8/2002 | Wang et al. | |
| 2003/0012701 A1 | 1/2003 | Sangha et al. | |
| 2003/0018495 A1 | 1/2003 | Sussman | |
| 2003/0136698 A1 | 7/2003 | Klatt | |
| 2003/0142784 A1 | 7/2003 | Suzuki et al. | |
| 2003/0174326 A1 * | 9/2003 | Rzasa et al. | 356/326 |
| 2003/0193185 A1 | 10/2003 | Valley et al. | |
| 2003/0200726 A1 | 10/2003 | Rast | |
| 2003/0209461 A1 | 11/2003 | French et al. | |
| 2004/0011806 A1 | 1/2004 | Luciano et al. | |
| 2004/0011961 A1 | 1/2004 | Platt et al. | |
| 2004/0045863 A1 | 3/2004 | Rhoades | |
| 2004/0069674 A1 | 4/2004 | Siegel | |
| 2004/0069675 A1 | 4/2004 | Stevens | |
| 2004/0088187 A1 | 5/2004 | Chudy et al. | |
| 2004/0094050 A1 * | 5/2004 | Ackley, Jr. et al. | 101/44 |
| 2004/0122713 A1 | 6/2004 | Hill, Sr. et al. | |
| 2004/0123564 A1 | 7/2004 | McErlean et al. | |
| 2004/0140241 A1 | 7/2004 | Weinstein | |
| 2004/0158507 A1 | 8/2004 | Meek et al. | |
| 2004/0162634 A1 | 8/2004 | Rice et al. | |
| 2004/0172295 A1 | 9/2004 | Dahlin et al. | |
| 2004/0188998 A1 | 9/2004 | Henthorn | |
| 2004/0217038 A1 | 11/2004 | Gibson | |
| 2004/0225528 A1 | 11/2004 | Brock | |
| 2004/0243445 A1 | 12/2004 | Keene | |
| 2004/0249591 A1 * | 12/2004 | Trebbi | 702/81 |
| 2004/0256277 A1 | 12/2004 | Gedanke | |
| 2004/0260424 A1 | 12/2004 | Mahar | |
| 2004/0268413 A1 | 12/2004 | Reid et al. | |
| 2005/0021367 A1 | 1/2005 | Saeger et al. | |
| 2005/0044762 A1 | 3/2005 | Alturim | |
| 2005/0049746 A1 | 3/2005 | Rosenblum | |
| 2005/0049747 A1 | 3/2005 | Willoughby et al. | |
| 2005/0060197 A1 | 3/2005 | Mayaud | |
| 2005/0061825 A1 | 3/2005 | Willoughby et al. | |
| 2005/0144038 A1 | 6/2005 | Tamblyn et al. | |
| 2005/0171813 A1 | 8/2005 | Jordan | |
| 2005/0209879 A1 | 9/2005 | Chalmers | |
| 2005/0218152 A1 | 10/2005 | Simon | |
| 2005/0269817 A1 | 12/2005 | Alasia et al. | |
| 2006/0045323 A1 * | 3/2006 | Ateya | 382/141 |
| 2006/0064670 A1 | 3/2006 | Linebarger et al. | |
| 2006/0065670 A1 | 3/2006 | Doublet et al. | |
| 2006/0076262 A1 | 4/2006 | Bassett | |
| 2006/0122729 A1 | 6/2006 | Murphy et al. | |
| 2006/0124502 A1 | 6/2006 | Lee | |
| 2006/0163269 A1 | 7/2006 | Anderson et al. | |
| 2006/0163869 A1 | 7/2006 | Adler et al. | |
| 2006/0213816 A1 | 9/2006 | Jorristsma | |
| 2006/0219595 A1 | 10/2006 | Peters | |
| 2007/0000805 A1 | 1/2007 | Van Den Brink | |
| 2007/0131576 A1 | 6/2007 | Ehling et al. | |
| 2007/0150219 A1 * | 6/2007 | Cawker et al. | 702/82 |
| 2007/0168228 A1 | 7/2007 | Lawless | |
| 2007/0173971 A1 | 7/2007 | Richardson et al. | |
| 2007/0210164 A1 | 9/2007 | Conlon et al. | |

(56) References Cited

U.S. PATENT DOCUMENTS

| | | |
|---|---|---|
| 2007/0228047 A1 | 10/2007 | Pehr et al. |
| 2007/0235369 A1 | 10/2007 | Perrell |
| 2008/0059228 A1 | 3/2008 | Bossi et al. |
| 2008/0110131 A1* | 5/2008 | Kim .............................. 53/154 |
| 2008/0142400 A1 | 6/2008 | Arnold |
| 2008/0190076 A1 | 8/2008 | Klingel et al. |
| 2008/0228160 A1 | 9/2008 | Harrison |
| 2009/0119129 A1 | 5/2009 | Nadas et al. |
| 2009/0133362 A1* | 5/2009 | Bentele et al. .................... 53/54 |
| 2009/0139893 A1 | 6/2009 | McGonagle et al. |
| 2009/0230013 A1 | 9/2009 | Born et al. |
| 2010/0069213 A1 | 3/2010 | Luciano et al. |
| 2010/0089936 A1 | 4/2010 | Luciano et al. |
| 2010/0100391 A1 | 4/2010 | Daya et al. |
| 2010/0139222 A1* | 6/2010 | Federle et al. .................. 53/474 |
| 2010/0147734 A1 | 6/2010 | Luciano, Jr. |
| 2010/0153129 A1 | 6/2010 | Luciano et al. |
| 2010/0175352 A1* | 7/2010 | Soloman ......................... 53/508 |
| 2010/0265072 A1 | 10/2010 | Goetz et al. |
| 2010/0287880 A1* | 11/2010 | Yasunaga et al. ................. 53/64 |
| 2010/0324728 A1 | 12/2010 | Rosenblum |
| 2011/0036856 A1 | 2/2011 | van Ooyen et al. |
| 2011/0040572 A1 | 2/2011 | Chmiel et al. |
| 2011/0100863 A1 | 5/2011 | Luciano |
| 2011/0101016 A1 | 5/2011 | Luciano, Jr. |
| 2011/0157342 A1* | 6/2011 | Kim ................................ 348/61 |
| 2011/0161097 A1 | 6/2011 | Fox et al. |
| 2011/0239587 A1* | 10/2011 | Yuyama et al. ......... B65B 5/103 53/131.4 |
| 2011/0251850 A1 | 10/2011 | Stephens |
| 2011/0264465 A1 | 10/2011 | Lindsay |
| 2012/0022893 A1 | 1/2012 | Findlay et al. |
| 2012/0089416 A1 | 4/2012 | Luciano, Jr. |
| 2012/0097560 A1 | 4/2012 | Contractor |
| 2012/0116579 A1 | 5/2012 | Shows et al. |
| 2012/0123907 A1 | 5/2012 | Luciano |
| 2012/0158430 A1 | 6/2012 | MacDonald |
| 2012/0186693 A1 | 7/2012 | Luciano et al. |
| 2012/0200596 A1* | 8/2012 | Gotou et al. .................. 345/625 |
| 2012/0290129 A1 | 11/2012 | Luciano et al. |
| 2012/0293623 A1* | 11/2012 | Nygaard ......................... 348/46 |
| 2012/0296592 A1 | 11/2012 | Luciano et al. |
| 2012/0312714 A1 | 12/2012 | Luciano et al. |
| 2013/0161207 A1 | 6/2013 | Luciano et al. |
| 2014/0002631 A1* | 1/2014 | Amano et al. .................. 348/86 |

FOREIGN PATENT DOCUMENTS

| | | | |
|---|---|---|---|
| WO | WO 2004/082561 A1 | 9/2004 | |
| WO | WO 2005/102841 | 11/2005 | |
| WO | WO 2011080462 A1 * | 7/2011 | ......... G01N 21/9508 |

* cited by examiner

INSPECTION SYSTEM AND METHOD WITH A CONTROL PROCESS THAT INSPECTS DIFFERENT MEDICATIONS

CROSS REFERENCE

This patent application claims the benefit of provisional patent application 61/486,427 entitled INSPECTION SYSTEM AND METHOD WITH A CONTROL PROCESS THAT INSPECTS DIFFERENT MEDICATIONS, and provisional patent application 61/486,436 filed entitled MULTIPLE INSPECTION SYSTEM AND METHOD THAT INSPECTS DIFFERENT MEDICATIONS, both filed on May 16, 2011, and this patent application is a continuation-in-part of patent application Ser. No. 13/357,483 entitled PILL ASSEMBLY FOR PILL PACKAGING AND DELIVERY SYSTEMS filed on Jan. 24, 2012, that claims the benefit of provisional patent application 60/615,267 having a filing date of Oct. 1, 2004, and this patent application is a continuation-in-part of patent application Ser. No. 11/241,783, now U.S. Pat. No. 8,123,036, entitled PILL ASSEMBLY FOR PILL PACKAGING AND DELIVERY SYSTEMS filed on Sep. 30, 2005, that claims the benefit of provisional patent application 60/615,267 having a filing date of Oct. 1, 2004, and this patent application is a continuation-in-part of patent application Ser. No. 13/312,907 filed on Dec. 6, 2011, now U.S. Pat. No. 9,015,058 entitled SYSTEM AND METHOD FOR MATRIX-BASED DOSAGE SCHEDULING, which claims the benefit of provisional patent application 61/420,140, and this patent application is a continuation-in-part of patent application Ser. No. 13/312,888 filed on Dec. 6, 2011, now U.S. Pat. No. 8,972,288 entitled SYSTEM AND METHOD FOR ONLINE MATRIX-BASED DOSAGE SCHEDULING, which claims the benefit of provisional patent application 61/420,151, and this patent application claims the benefit of provisional patent application 61/498,489 filed on Jun. 17, 2011, and this patent application is a continuation-in-part of patent application Ser. No. 12/945,709 filed on Nov. 12, 2010 now U.S. Pat. No. 9,141,764 entitled SYSTEM AND METHOD FOR ONLINE INTEGRATED MULTIPLE TABLET ORDERING, and this patent application is a continuation-in-part of patent application Ser. No. 12/896,284 filed on Oct. 1, 2010 entitled SYSTEM AND METHOD FOR GENERATING AN INTEGRATED LABEL FOR CONTAINER HOUSING MULTI-SCRIPT POUCHES that claims the benefit of provisional patent application 61/248,471 filed on Oct. 4, 2009, and this patent application is a continuation-in-part of patent application Ser. No. 12/896,275 filed on Oct. 1, 2010 now U.S. Pat. No. 8,914,298 entitled SYSTEM AND METHOD FOR INTEGRATED VERIFICATION AND ASSEMBLY OF MULTI-SCRIPT POUCHES INTO A HOUSING CONTAINER that claims the benefit of provisional patent application 61/248,471 filed on Oct. 4, 2009, and this patent application is a continuation-in-part of patent application Ser. No. 12/896,134 filed on Oct. 1, 2010 now U.S. Pat. No. 8,712,582 entitled SYSTEM AND METHOD FOR COMBING DIFFERENT TABLETS INTO A POUCH that claims the benefit of provisional patent application 61/248,471 filed on Oct. 4, 2009, and this patent application is a continuation-in-part of patent application Ser. No. 12/891,042 filed on Sep. 27, 2010 entitled LOW VISION PATIENT COMPLIANT MEDICATION MANAGEMENT SYSTEM AND METHOD that claims the benefit of provisional patent application 61/245,912 filed on Sep. 25, 2009, and this patent application is a continuation-in-part of patent application Ser. No. 12/891,029 filed on Sep. 27, 2010 entitled DUAL DISPENSING TABLET CONTAINER that claims the benefit of provisional patent application 61/245,899 filed on Sep. 25, 2009, and this patent application is a continuation-in-part of patent application Ser. No. 12/696,884 filed on Jan. 29, 2010 now U.S. Pat. No. 8,931,241 entitled SYSTEM AND METHOD FOR VERIFYING ANS ASSEMBLING A MULTIPLE PRESCRIPTION PACKAGE that claims the benefit of provisional patent application 60/854,341 filed on Oct. 24, 2006, and this patent application is a continuation-in-part of patent application Ser. No. 12/684,640 filed on Jan. 8, 2010 entitled USER SELECTABLE MULTIPLE TABLET PACKAGE, and this patent application is a continuation-in-part of patent application Ser. No. 12/684,664 filed on Jan. 8, 2010 entitled SYSTEM AND METHOD FOR PLACING A MULTIPLE TABLET ORDER, and this patent application is a continuation-in-part of patent application Ser. No. 12/684,060 filed on Jan. 7, 2010 entitled SYSTEM AND METHOD FOR AUTOMATICALLY MANAGING INVENTORY IN A MULTIPLE TABLE PACKAGE which is a continuation-in-part of patent application Ser. No. 11/796,123 now U.S. Pat. No. 7,690,173, filed on Apr. 25, 2007 entitled MULTIPLE PRESCRIPTION PRODUCTION FACILITY, and this patent application is a continuation-in-part of patent application Ser. No. 12/631,586 filed on Dec. 4, 2009 now U.S. Pat. No. 8,777,012 entitled MULTIPLE PRESCRIPTION PRODUCTION FACILITY, and this patent application is a continuation-in-part of patent application Ser. No. 12/424,483 filed on Apr. 15, 2009 entitled MANUFACTURING SEPARABLE POUCHES WITH A CENTER CUT BLADE, and this patent application is a continuation-in-part of patent application Ser. No. 12/424,475 now U.S. Pat. No. 8,146,747, filed on Apr. 15, 2009 entitled TABLET DISPENSING CONTAINER that claims the benefit of provisional patent application 61/045,160 filed Apr. 15, 2008, provisional patent application 61/045,166 filed Apr. 15, 2008, provisional patent application 61/045,171 filed Apr. 15, 2008, and this patent application is a continuation-in-part of patent application Ser. No. 12/418,436 filed on Apr. 3, 2009 now abandoned entitled CHILD PROOF MEDICATION PACKAGING SYSTEM AND METHOD, and this patent application is a continuation-in-part of patent application Ser. No. 11/796,125 filed on Apr. 25, 2007 entitled SYSTEM AND METHOD FOR PROCESSING A MULTIPLE PRESCRIPTION ORDER, and this patent application is a continuation-in-part of patent application Ser. No. 12/418,422 filed on Apr. 3, 2009 entitled PATIENT COMPLIANT MEDICATION MANAGEMENT SYSTEM AND METHOD that claims the benefit of provisional patent application 61/042,262 filed Apr. 3, 2008 and provisional patent application 61/042,263 filed on Apr. 3, 2008, and this patent application is a continuation-in-part of patent application Ser. No. 11/923,321 filed on Oct. 24, 2007 entitled METHOD FOR VERIFYING AND ASSEMBLING A MULTIPLE PRESCRIPTION PACKAGE that claims the benefit of provisional patent application 60/854,341 having a filing date of Oct. 24, 2006, and this patent application is a continuation-in-part of patent application Ser. No. 11/796,124 entitled MULTIPLE PRESCRIPTION PACKAGE AND METHOD FOR FILING THE PACKAGE that claims the benefit of provisional patent applications 60/795,370, 60/795,446, and 60/795,413 all having a filing date of Apr. 26, 2006, and all applications listed are hereby incorporated by reference.

FIELD

This description relates to an inspection system and method with an inspection control process that controls the inspection processes of different medications. More particularly, the description relates to an inspection result state selected by the inspection control process module, wherein the inspection result state includes a positive inspection result state, a negative inspection result state, and an inconclusive inspection result state.

BACKGROUND

Patients struggle with remembering which medications to take and when to take them. This is particularly a problem for the elderly or infirm. Additionally, the more severe the medical problem, the more challenging it is to take medications properly. To address this problem, various manual devices exist that have multiple compartments that patients (or their care-givers) pre-populate with medications corresponding to various dosing periods. Although this helps reduce errors, the containers are unwieldy and still prone to filling errors.

Automated filling machines have been developed to combine medications into a single pouch or blister that, in turn, are connected to other pouches or containers. Some automated filling machines are capable of filling packages with a variety of different pharmaceuticals or nutraceuticals that are consumed by a patient at the same time. Some patients may have multiple packages or containers that are associated with multiple dosing periods during the day. For example, there may be a group of tablets that are consumed before breakfast in one container, another container may have a group of medications that are to be consumed with lunch, and yet another group of medications that are to be taken before going to bed.

Generally, automated tablet inspection is limited in scope (normally to a single tablet type) and in other cases fail to accurately confirm the proper medication when a multiplicity of medications are placed in a single package or container.

The problem with using most technically and financially viable automated inspection techniques is that the uncertainty percentage is generally unacceptably high, causing a prohibitively expensive and slow manual inspection process to be invoked.

Although it may be seen that packaging multiple medications into containers that hold all medications to be consumed at the same time is a desirable product, large scale implementations have been limited by the lack of a sufficiently reliable and cost-effect way of automatically inspecting filled containers to assure that they are properly filled.

Thus, it would be beneficial to accurately fill containers having a variety of different medications or supplements. Additionally, compliance with a regimen of medication or supplements is challenging for patients having difficulty remembering when a dose has been consumed. The problem is exacerbated by the number of tablets being consumed increasing as the patient ages.

SUMMARY

An inspection system and method that inspects at least two different medications is described. The inspection system includes an automated filling station or system, an automated inspection station or system, a measurement device or measurement means, an inspection control process module, an expected medication value, and an inspection result state. The automated filling station houses at least two different medications. The automated inspection station receives the medications associated with one of the packages. The measurement device associated with the automated inspection station is configured to examine the different medications and generate a measured medication value for the different medications.

In operation, the inspection control process receives information about the intended contents of each filled package, along with the physical properties that are to be measured. In one illustrative embodiment, the inspection control process module receives results, which are then analyzed.

In general, the inspection control process module is communicatively coupled to the automated filling station and the automated inspection station. The measured medication value is received by the inspection control process module. Additionally, the expected medication value is received by the inspection control process module. The inspection result state is then selected by the inspection control process module by comparing the expected medication value to the measured medication value. The inspection result state includes at least one of a positive inspection result state, a negative inspection result state, and an inconclusive inspection result state.

In one embodiment, the measurement device examines the different medications before the automated filling station fills each package with the different medications. In another embodiment, the measurement device examines the different medications after the automated filling station fills each package with the different medications.

In yet another illustrative embodiment, the inspection system includes two measurements devices. The first measurement device examines the different medications before the automated filling station fills each package with the different medications. The second measurement device examines the different medications after the automated filling station fills each package with different medications.

Additionally, an embodiment in which the automated filling station is configured to house the automated inspection station, the measurement device, and the inspection control process module is described.

Furthermore, a stand-alone inspection embodiment is described that includes the automated inspection station, the measurement device, and the inspection control process module. In this embodiment, the stand-alone inspection station housing is communicatively coupled to the automated filling station.

Further still, an embodiment where the measurement device is housed by the automated inspection station is described. In this embodiment, the stand-alone inspection control process module is communicatively coupled to the inspection station and the automated filling station.

Further yet, an embodiment where the process control module is communicatively coupled to the automated filling station, the automated inspection station, and the inspection control module is described. In this embodiment, the process control module is configured to convey the medications according to the inspection result state.

DRAWINGS

The present invention will be more fully understood by reference to the following drawings which are for illustrative, not limiting, purposes.

Figure 8:
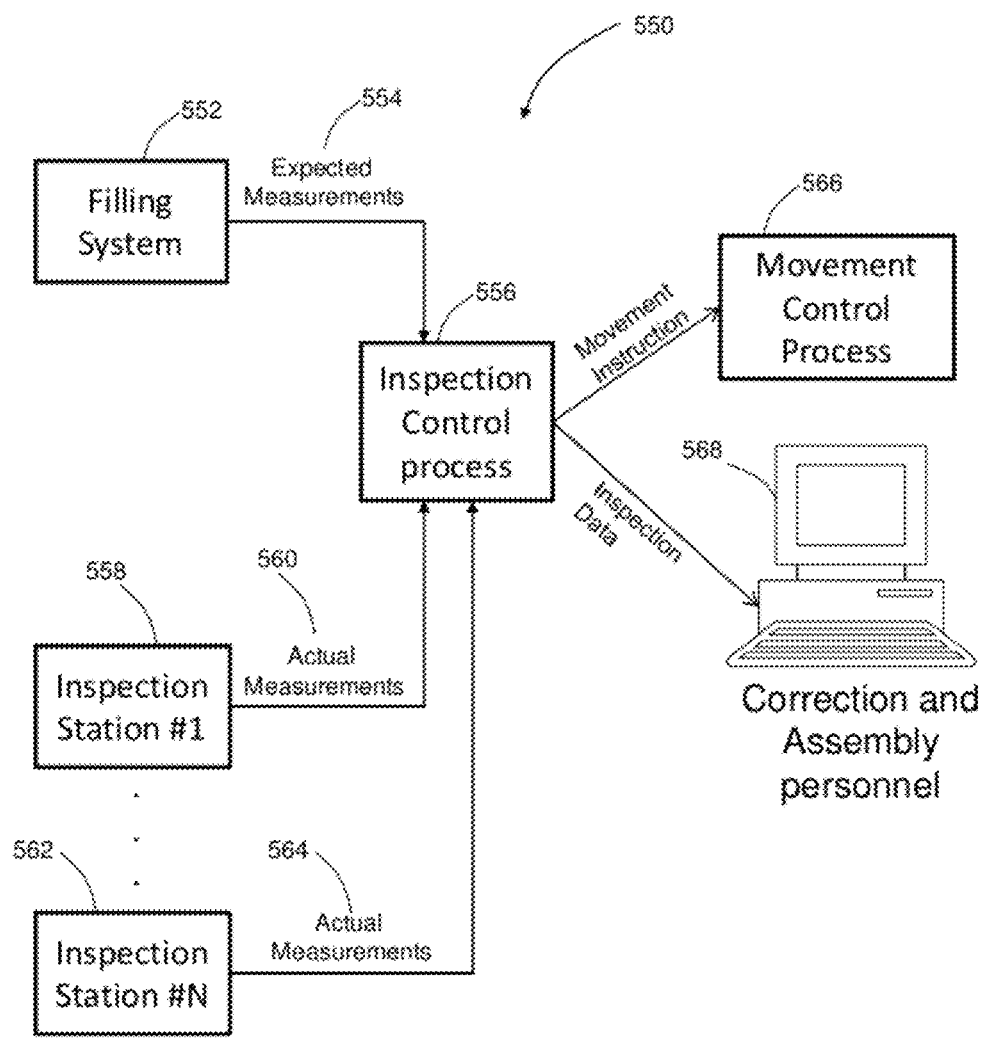

FIG. 8 shown a stand-alone inspection control process system.

Figure 9A:
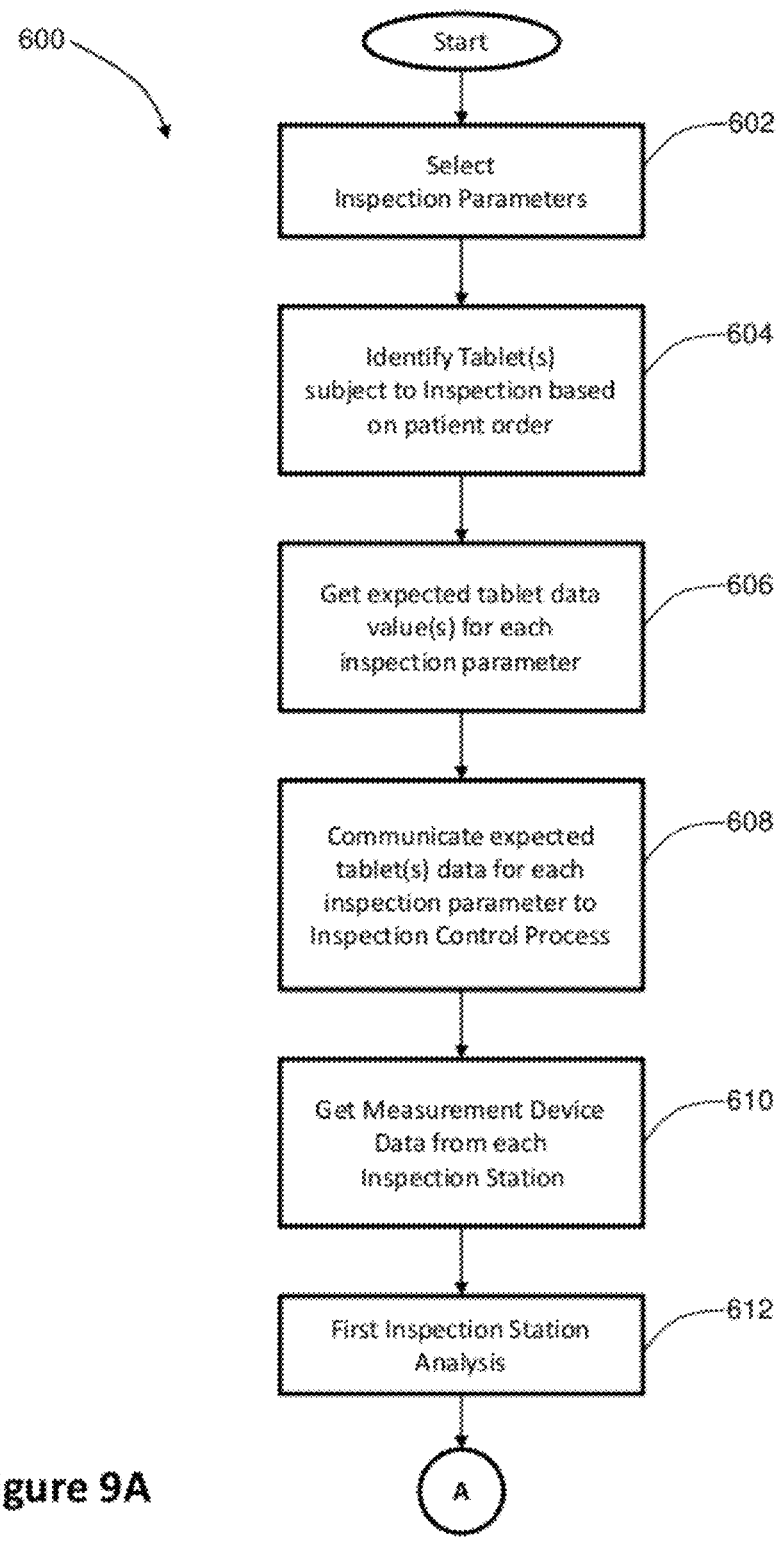
Figure 9B:
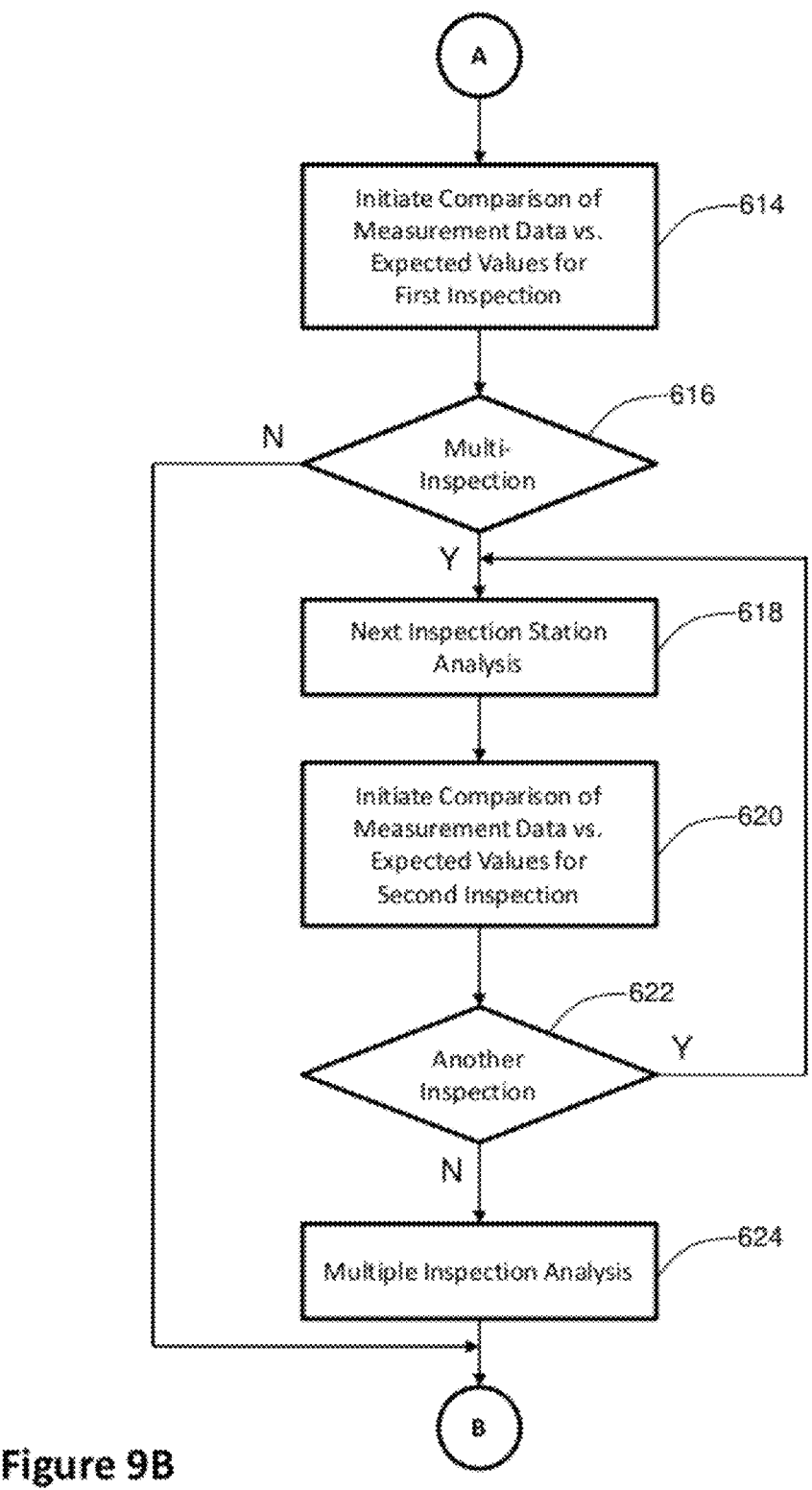
Figure 9C:
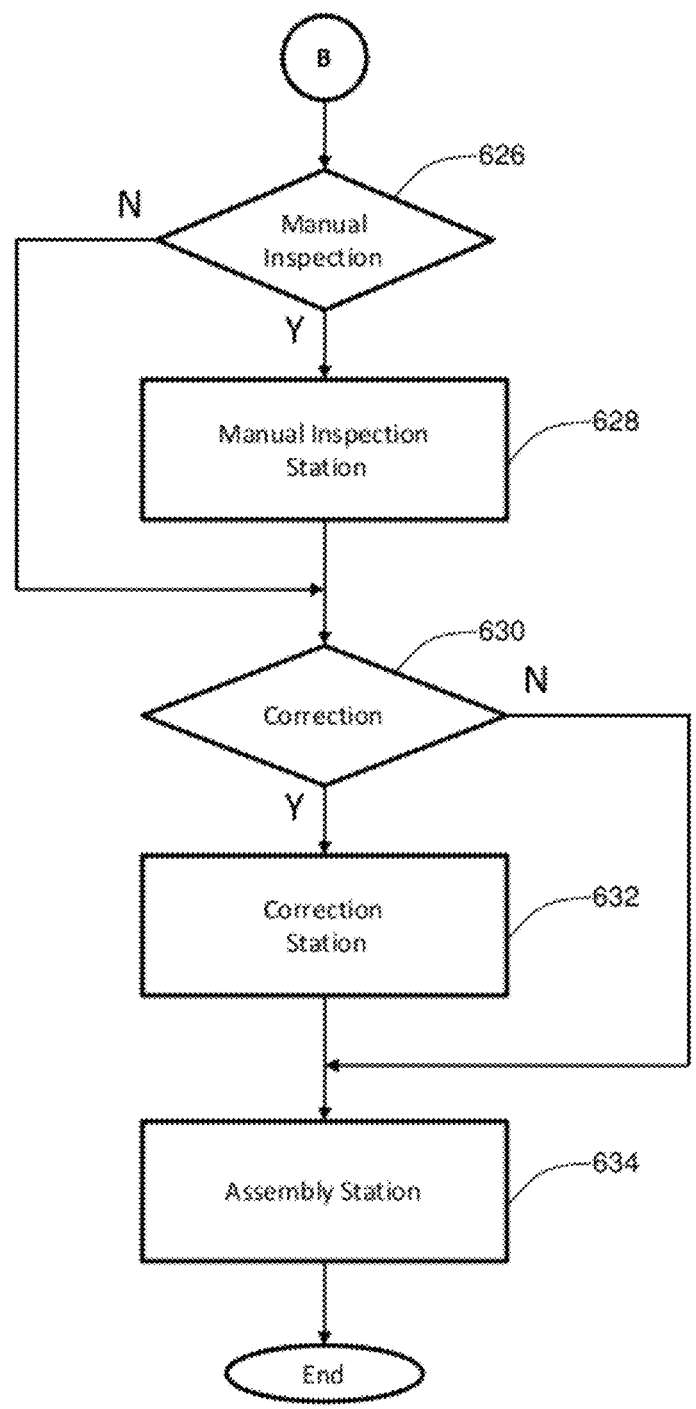

FIGS. 9A-9C show an inspection and multi-inspection method that inspects preliminary packages that include one or more medications.

Figure 10:
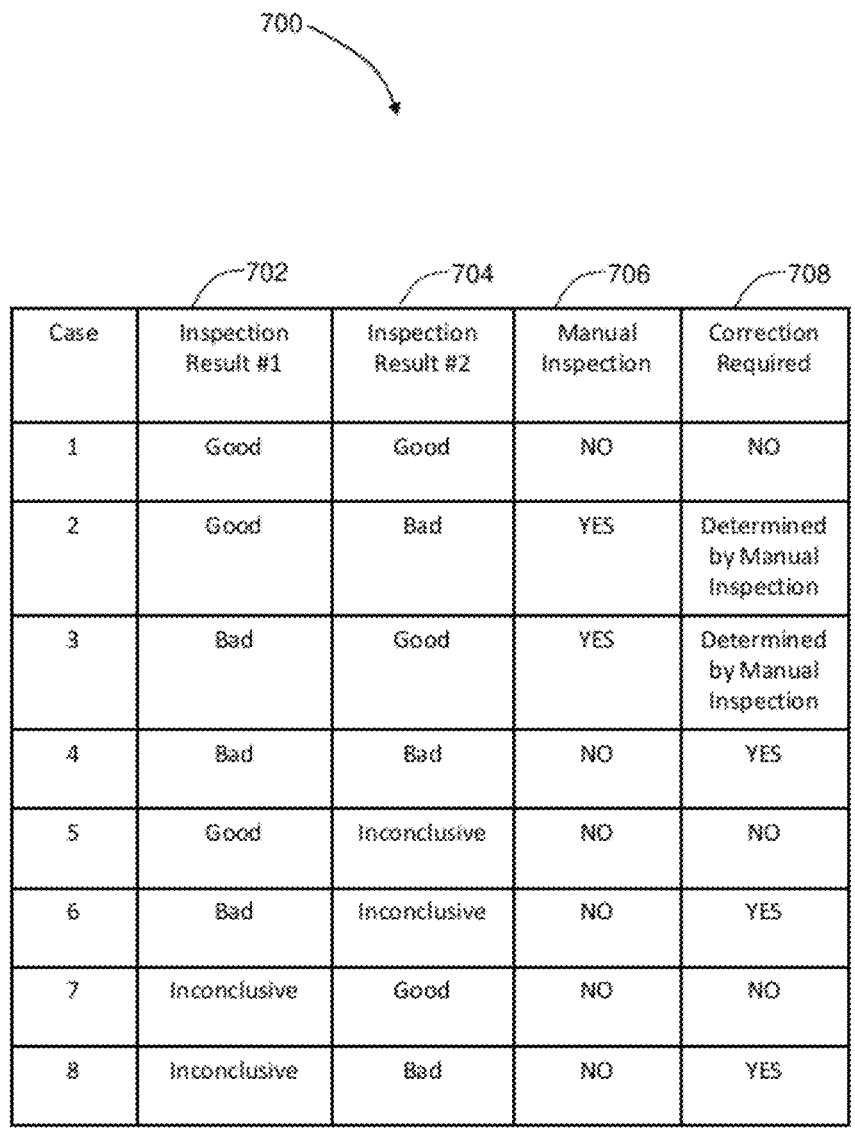

FIG. 10 shows a decision table for the multi-inspection analysis of two inspection stations.

Figure 11:
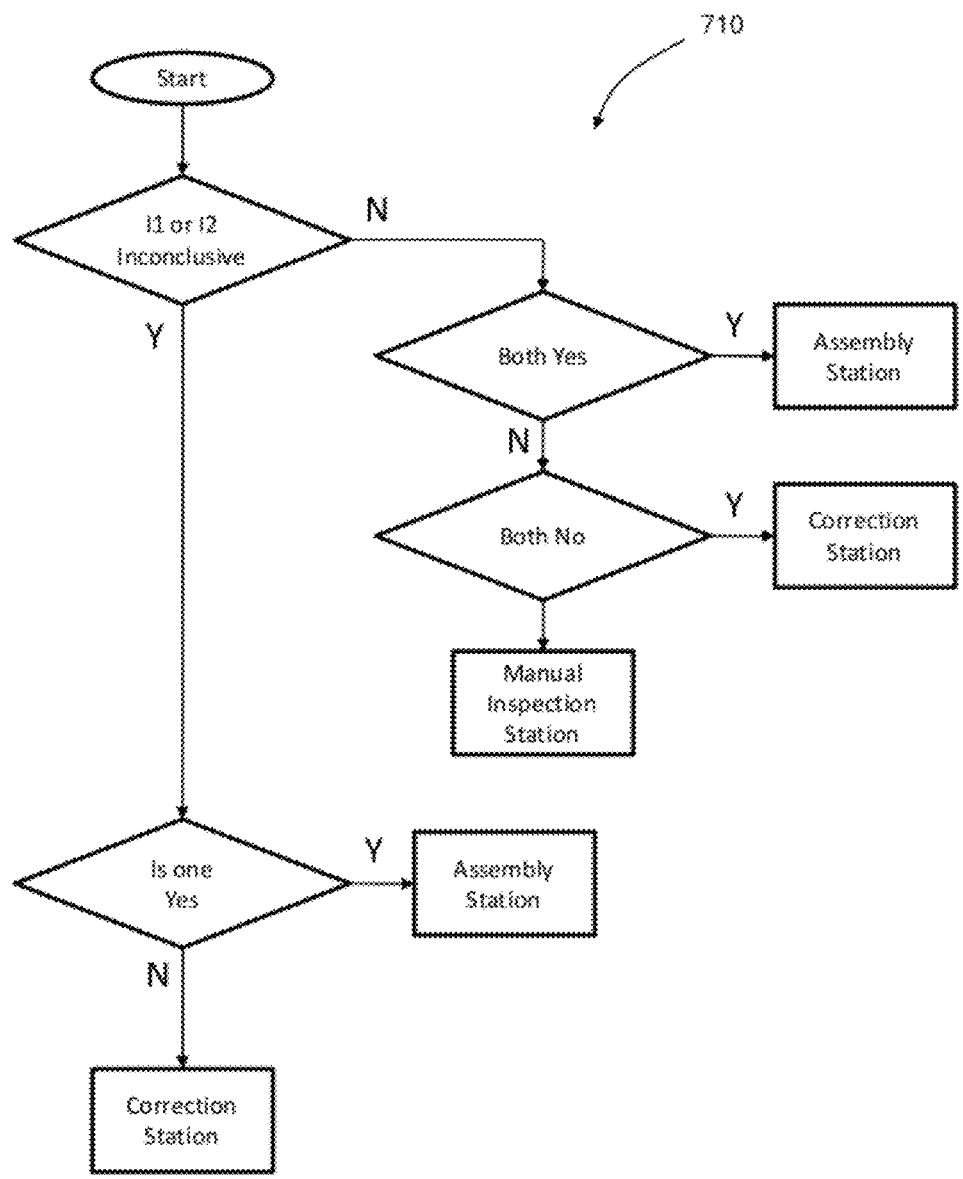

FIG. 11 shows a sequential flowchart of the decision table in FIG. 10.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the methods may vary as to details, order of the actions, or other variations without departing from the illustrative methods disclosed herein.

An inspection system and method is described that assures proper packaging of multiple medications into individualized, time-specific packages. More particularly, the inspection system includes an inspection control process that coordinates the various aspects of a single inspection process, a multi-inspection process, and post-inspection processes.

The medications include, but are not limited to, pharmaceuticals, nutraceuticals, vitamins, supplements, tablets, caplets, capsules, with prescription, without prescription, and any other medication that can be packaged in a preliminary package, package, or container. For purposes of the illustrative embodiments presented herein, the terms medication and tablets are used interchangeably.

For purposes of this patent, the terms preliminary package, package, and container are used interchangeably. Illustrative preliminary packages include a pouch, blister, vial, or any package that holds or houses a plurality of different medications. A preliminary package may exist in a sealed preliminary package, e.g. pouch, or an unsealed preliminary package, e.g. blister. The preliminary packages are then placed into a "final" package such as a box container or sleeve.

The illustrative inspection systems and methods described herein include multiple inspection stations, in which each inspection station generates an inspection result state that is analyzed by a multi-inspection analytical module. In one embodiment, the multi-inspection analytical module is associated with an inspection control process module.

In general, the inspection station compares the expected medication value to the measured medication value to generate an inspection result state. The inspection result state includes a positive inspection result state, a negative inspection result state, and an inconclusive inspection result state. The inspection result state may be associated with identifying that a tablet or medication is broken, compromised, or there are too many tablets being dispensed at one particular time in a particular package.

At least two inspection result states are then analyzed by the multi-inspection analytical module. The multi-inspection analytical module then proceeds to select one of a plurality of post-inspection states that convey the package to one of a manual inspection station, a correction station, or an assembly station.

By analyzing two or more inspection processes, the systems and methods described herein reduce the uncertainty about the correctness of the container filling and improve accuracy. The two or more inspection processes may be physically combined in the same housing or may operate as separate physical inspection stations. In the illustrative embodiment, the multiple inspection analysis operates by using a decision table to determine the post-inspection state.

The inspection may be conducted by measuring the physical characteristics of tablets using analytical methods, including but not limited to, 2D visual light sensor (camera or video), 3D visual light sensor, precision weighing, X-ray, near infrared, magnetic resonance imaging, ultrasound, laser excitation, raman spectroscopy, fluorescence spectroscopy, and other such analytical chemical methods. Additionally, precision counting systems that employ a sensor with a photo resistor to detect a light beam broken by a tablet may also be used as an inspection process. Furthermore, an inspection station may be dedicated to identifying RFID codes or other such machine readable representation of data associated with one or more medications or tablets.

The illustrative inspection properties provide quantitative results or qualitative results. Qualitative inspection properties ask the basic question of "what" is present. Quantitative inspection properties ask the basic question of "how much" of each. Qualitative analysis gives an indication of the identity of the chemical species in a sample. Quantitative analysis determines the amount of each compound. Additionally, as described herein, algorithmic processes can be applied to qualitative measurements that result in a quantitative value. For example, an optical system relying on visible light performs a quantitative analysis of tablet size, shape, and color. An algorithm may then be applied that would count the number of tablets, thereby providing a quantitative measurement.

Figure 1A:
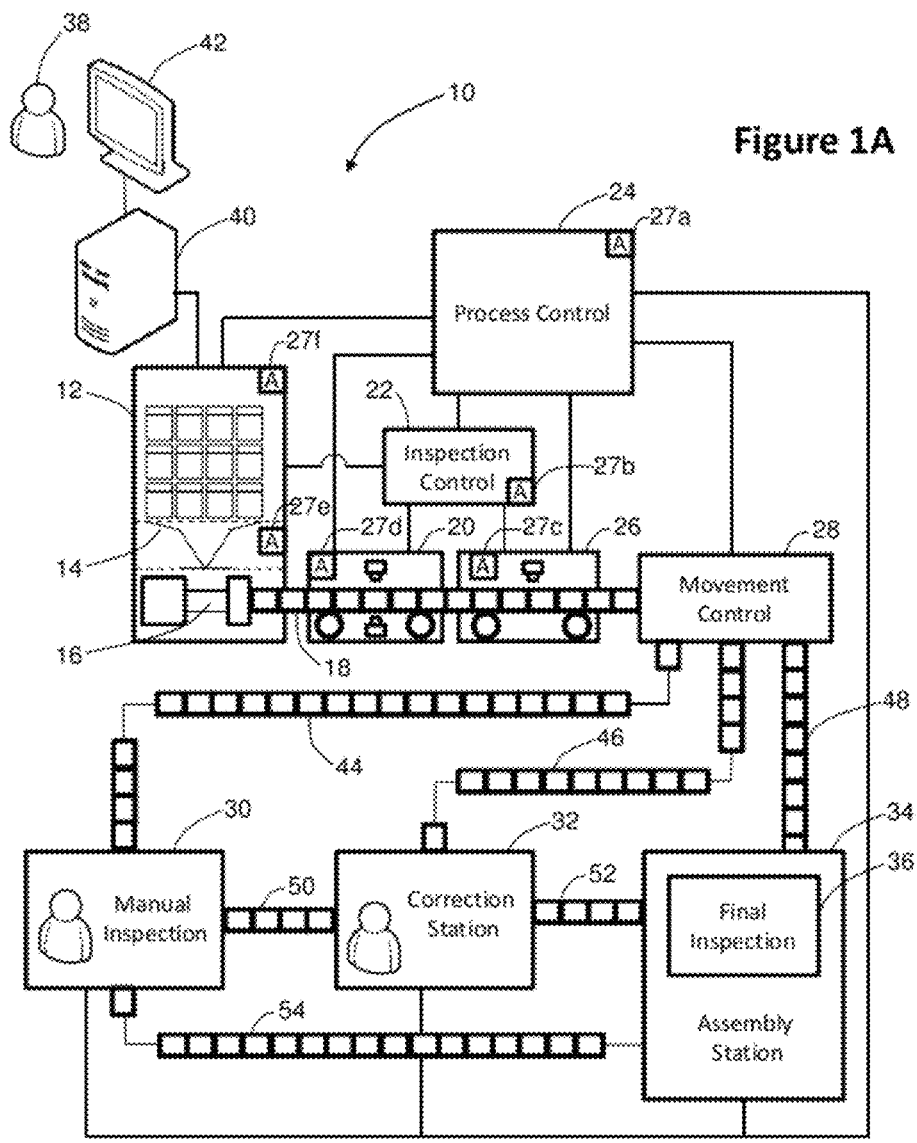
FIG. 1A shows a multiple inspection system for inspecting different medications in a preliminary package.
Figure 1B:
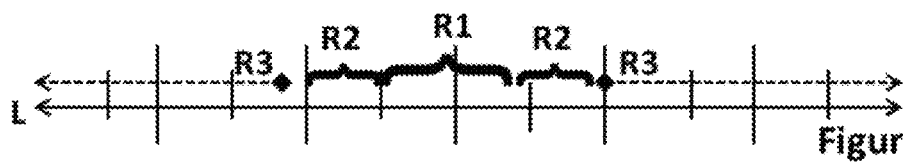
FIG. 1B shows an infinite line with the three states that form a complete set of possible values.

Referring to FIG. 1 there is shown an illustrative multiple inspection system 10 for inspecting different medications in a preliminary package. The multiple inspection system includes an automated filling station 12 that fills preliminary packages with different medications. The automated filling station 12 supplies at least two different medications.

An illustrative first automated inspection station 14 is housed within the automated filling station 12. The illustrative first automated inspection station 14 inspects the tablets before the tablets are placed in the preliminary packages. Alternatively, the first inspection station may be performed after the tablets are placed in the preliminary package.

The illustrative inspection station 14 includes a measurement device that examines the different medications and generates a measured medication value for the different medications. By way of example and not of limitation, the illustrative first automated inspection includes a hopper and a precision weighing device described in further detail in FIG. 3 below. In operation, the hopper catches the tablets and the tablets are then weighed with the precision weighing device. The measured medication value for the illustrative embodiment is the combined weight of the tablets.

An inspection control process module 22 receives the measured medication value (e.g. total weight of tablets) from the first inspection station 14. The inspection control process module 22 is communicatively coupled to the automated filling station 12. In operation, the measured medication value from the first inspection station 14 is received by the inspection control process module 22.

Although the inspection control process module 22 is shown as being separate from the automated filling station 12 housing the first automated inspection 14, the inspection control process module 22 may also be housed within the automated filling station 12. The inspection result state is selected by the inspection control process module 22, which compares the expected medication value to the measured medication value.

In the illustrative embodiment, the inspection result state includes a positive inspection result state, a negative inspection result state, and an inconclusive inspection result state. The three states form a complete set of possible values that are represented by the infinite line L in FIG. 1B. The positive inspection result state corresponds to the measured medication value being a set of values within a small range that approximates the expected medication value represented by R1. The inconclusive inspection result state corresponds to a set of values on either side of the expected medication value range represented by R2. The negative inspection result state corresponds to any measured medication value being outside the range made up of the expected medication value range and the inconclusive inspection result range, and is represented by dashed lines R3.

After the first inspection station 14, a preliminary packaging component 16 receives the multiple medications, combines the multiple medications, and places the medications within the preliminary package. In the illustrative pouch embodiment, the pouch is sealed by the preliminary packaging component 16, as described in patent application Ser. No. 11/923,321 entitled A METHOD FOR VERIFYING AND ASSEMBLING A MULTIPLE PRESCRIPTION PACKAGE that is hereby incorporated by reference. For the blister packaging embodiment, the blister is filled with the different medications; the blister may be sealed at the preliminary packaging station or may be sealed at a later time as described in patent application Ser. No. 11/796,124 entitled MULTIPLE PRESCRIPTION PACKAGE AND METHOD FOR FILLING PACKAGE that is hereby incorporated by reference.

The illustrative filling station 12 inspects the medications that have been placed in the preliminary packages. The type of inspection depends on the particular design of the filling station 12 or inspection station as described above.

A conveyor 18 then receives and conveys the preliminary packages to a second inspection station 20. The illustrative conveyor performs the material handling of transferring goods from one location to another. Conveyance means includes materials handling equipment that conveys goods from one location to another. Illustrative conveyor systems include belt conveyors, wire mesh conveyors, pharmaceutical conveyors, and other such conveyors capable of transferring preliminary packages.

By way of example and not of limitation, the second inspection station 20 performs an optical examination of tablets within sealed or unsealed preliminary packages. The optical examination includes one or more camera or video sensors that capture a plurality of images. The images represent the measured medication value and are qualitative results, i.e. they represent "what" and not "how much." The captured images are then compared to the expected medication value.

The expected medication value for the illustrative optical examination includes a collection of training data or samples that may include "clean" images of each tablet taken under controlled conditions. The clean images are used to establish a full set of values comprising a range, such as that represented by L in FIG. 1B, that can be used for comparison purposes. Additionally, the training data may include a variety of perspective views of the multiple images of each tablet.

An algorithm then analyzes the captured images, i.e. measured medication value, the training data, i.e. expected medication value, and then classifies the captured images as being associated with a particular medication. By way of example and not of limitation, an algorithm can match the size, color, and shape of each medication and obtain a qualitative result.

The algorithms may then be tested to determine an error rate. The error rate is determined by the number of missed detections or false alarms. A missed detection occurs when samples that are categorized as being "correct" are incorrect. A false alarm occurs when samples are identified as being "incorrect" when they are actually correct. Depending on the weight given to either missed detection or false alarms, missed detections may have a significant impact, whereas false alarms may be costly but are otherwise harmless. Generally, the algorithmic processes described herein are iterative so that there may be modifications to system calibrations, algorithm weighting, and corresponding thresholds.

In the illustrative embodiment, the second inspection station 20 is communicatively coupled to an inspection control process module 22. In operation, the measured medication value from the second inspection station 20 and the expected medication value are received by the inspection control process module 22. The inspection control process module 22 is configured to perform the algorithmic analysis.

The operations of inspection process module 22 may occur in an integrated stand-alone inspection device that is independent of the filling station 12, but is communicatively coupled to the filling station. Thus, in an integrated stand-alone inspection embodiment, the stand-alone inspection station includes the second automated inspection station 20, the measurement device, and the inspection control process module 22.

Alternatively, the operations of the inspection process module 22 may be integrated into the filling station 12 (not shown). In this dual inspection filling station embodiment, the filling station performs a first inspection 14 before filling the preliminary package, and a second inspection 20 after the preliminary packages are filled.

After performing the optical examination and analyzing the measured medication value (captured images) and the expected medication value (training data), an inspection result state is selected by the inspection control process module 22. The inspection result states include a positive inspection result state, a negative inspection result state, and an inconclusive inspection result state.

The inspection control process module 22 is communicatively coupled to a process control module 24. The process control module 24 controls the movements and interrelationships between the system components and modules. Additionally, the process control module 24 directs the conveyance of the preliminary packages through the filling station, inspection stations, and post-inspection stations.

In the illustrative embodiment, the process control module 24 is communicatively coupled to the automated filling station 12, the first inspection station 14, the conveyor 18, the second inspection station 20, and the inspection control module 22. The process control module 24 controls the conveyance means described herein. Additionally, the process control module 24 conveys the medications according to the inspection result state. Thus, the process control module 24 is configured by hardware and software to provide real-time control and coordination of the various components of the inspection system.

A third inspection station 26 is in communication with the process control module 24. The illustrative third inspection station is an X-ray inspection. By way of example and not of limitation, the X-ray inspection station may operate as described in U.S. Pat. No. 6,324,253 that is hereby incorporated by reference.

The X-ray inspection process is similar to the optical examination described above. For example, the X-ray inspection includes one or more X-ray generators and X-ray detection components that capture X-ray images. Like the optical examination, the captured X-ray images are then compared to the expected medication X-ray images. An algorithm then analyzes the captured images and the training data, and classifies the captured images as being associated with a particular medication.

By way of example and not of limitation, an X-ray algorithm can match the size and shape of each medication and obtain a qualitative result. The optical examination may use color and shape to obtain a qualitative result. This qualitative algorithm may be distinguishable from a quantitative algorithm, as described above. The algorithms may then be tested to determine an error rate. The algorithmic processes are iterative so that there may be modifications to system calibrations, algorithm weighting, and corresponding thresholds.

After performing the X-ray examination, an inspection result state is selected by the inspection control process module 22. The inspection result states include a positive inspection result state, a negative inspection result state, and an inconclusive inspection result state. Each of these different states has a range of values that are along a complete spectrum of the possible results in a manner similar to the ranges described with respect to FIG. 1B. Additional inspection stations may also be included in the inspection system described above.

An analytical module 27 then proceeds to perform a multi-inspection analysis that compares the inspection results. The analytical module 27 performs a multi-inspection analysis of two or more automated inspection results for each preliminary package. After completing the multi-inspection analysis, the analytical module 27 selects one of a plurality of post-inspection states that is communicated to the process control module.

In the illustrative embodiment, the analytical module 27 communicates with the process control module 24. The multi-inspection analysis determines the appropriate post inspection state for each package. The post inspection states include a manual inspection station state, a correction station state, and an assembly station state.

The process control module 24 determines where to convey each package according to the multi-inspection analysis and the post inspection state. The post inspection state is communicated to the movement control module 28 that mechanically selects the appropriate post-inspection station.

The manual inspection state results in an instruction to the movement control module 28 to transfer the preliminary package to the manual inspection station 30. Also, the correction station state results in an instruction to the movement control module 28 to transfer the preliminary package to the correction station 32. Additionally, the assembly station state results in an instruction to the movement control module 28 to transfer the preliminary package to an assembly station 34 that includes a final inspection component 36.

In operation, an operator 38 inputs a multiple prescription order through a front-end pharmacy system operating on computer 40 and display 42 that is communicatively coupled to filling station 12. The illustrative software front end is a Pharmaserv™ pharmacy system or EPPA system, as described in patent application Ser. No. 12/896,275 entitled SYSTEM AND METHOD FOR INTEGRATED VERIFICATION AND ASSEMBLY OF MULTI-SCRIPT POUCHES INTO A HOUSING CONTAINER that is hereby incorporated by reference. The operator may be a patient, a caregiver, a nurse, a technician, a pharmacist, physician, or other such person qualified to use front-end pharmacy systems.

The movement control module 28 controls the physical conveyance of the various packages and containers throughout the inspection system 10. Generally, the movement control module 28 is associated with the process control module 24. For illustrative purposes, the movement control module 28 is presented as a separate component that receives the preliminary package from conveyor 18 and selects the manual inspection conveyor 44, correction station conveyor 46, or assembly station conveyor 48.

If the manual inspection conveyor 44 is selected, the preliminary package proceeds to manual inspection 30 where an operator manually inspects the package. The manual inspection operator then decides to convey the preliminary package to either the correction station 32 or assembly station 34 via manual inspection conveyor 50 or manual inspection conveyor 54, respectively. The manual inspection station conveyor 50 transports the manually inspected preliminary packages to correction station 32. The manual inspection conveyor 54 bypasses the correction station 32 and conveys the preliminary packages to assembly station 34. Additionally, the correction station conveyor 52 transfers the corrected preliminary packages to the assembly station 34.

In one embodiment, an instruction from the process control module that the package was improperly filled results in conveying the package to the manual inspection station and then conveying the package to one of the correction station and the assembly station. In another embodiment, the improperly filled instruction conveys the package to the correction station and then the assembly station. In yet another embodiment, a properly filled instruction is received by the process control module, and the package is conveyed to the assembly station.

After completing the post-inspection processes, the assembly station 34 generates the detailed label and other labels having the plurality of written information, as described in patent application Ser. No. 12/424,483 entitled MANUFACTURED SEPARABLE POUCHES WITH A CENTER CUT BLADE that is hereby incorporated by reference. The written information may also comprise packaging information. The written information may comprise information about each substance, appropriate labeling, summary information, a drug interaction report, or a combination thereof.

Figure 2:
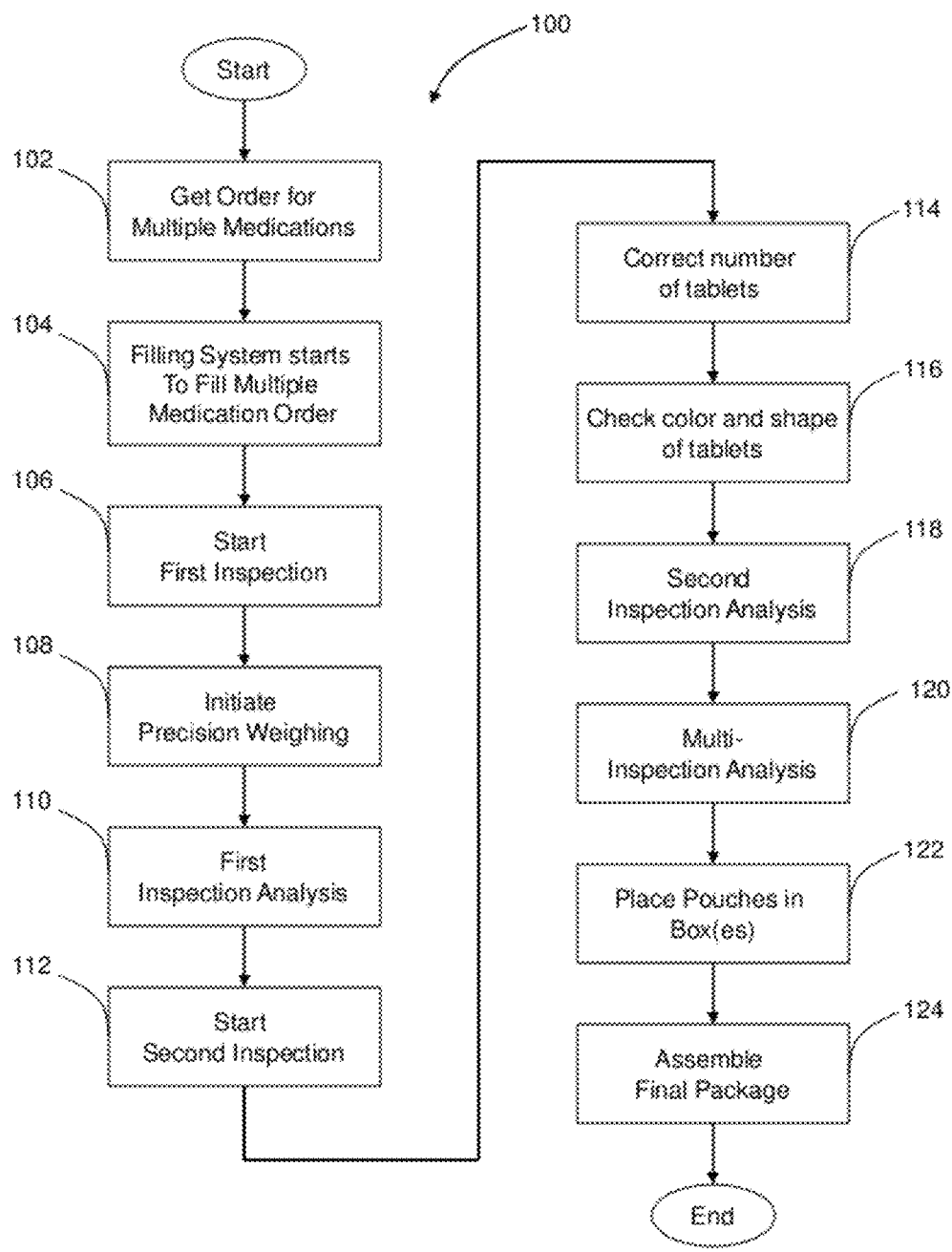
FIG. 2 shows a multiple step inspection method that inspects packages filled with at least two different medications that are to be consumed by a particular patient.

Referring to FIG. 2, there is shown a multiple inspection method that inspects packages filled with at least two different medications that are to be consumed by a particular patient. The illustrative method is initiated at block 102 when an order for multiple medications is received by the filling system. In the illustrative embodiment, a verified prescription order is received. The verified prescription order is an order that has been verified according to local jurisdictional requirements, insurance requirements, co-pay requirements, transactional requirements, or a combination thereof. For example, in certain jurisdictions a verified prescription order may require a medical doctor's signature, and may have to be processed by a pharmacist. Additionally, a verified order may require approval from an insurance company, Medicare, or any such entity. In other jurisdictions, the only form of verification may include confirming that funds are available from the particular individual or organization charged, which satisfies transactional requirements. By way of example and not of limitation, verification of the availability of funds may include simply receiving authorization to charge a credit card and confirming that the credit card is a valid card. Alternatively, an order may be received for supplements, as described in patent application Ser. No. 12/945,709 entitled SYSTEM AND METHOD FOR ONLINE INTEGRATED MULTIPLE TABLET ORDERING.

At block 104, the filling system starts to fill the multiple medication order. Each package is filled with at least two different medications by the filling station. The filling system is configured to associate at least one package with the patient. The filling process includes placing the medications in a blister package that is unsealed or placing the medications in a pouch that is sealed. Additionally, the blister package may also be sealed in the filling machine.

The method then proceeds to select each package that is to be inspected. In the illustrative embodiment, the process control selects the package and the inspection process. The process control module is communicatively coupled to the filling station.

At block 106, the first inspection is initiated. The first inspection may be qualitative or quantitative. By way of example of not of limitation, the illustrative first inspection step is a precision weighing process as shown in block 108.

The first automated inspection is initiated by examining the different medications with a first measurement device that is associated with a first inspection property. Subsequently, a comparison of a first-expected inspection value with the first measurement result generates the first inspection result state.

In the illustrative embodiment, the first inspection analysis is performed by the inspection control process 22 at block 110. As previously described, the inspection control process module 22 receives the measured medication value from the first inspection station 14. Additionally, the expected medication value is received by the inspection control process module 22. The inspection result state is then selected by the inspection control process module 22. The inspection control module compares the expected medication value to the measured medication value to generate the inspection result state, which includes a positive inspection result state, a negative inspection result state, and an inconclusive inspection result state.

As previously described, the positive inspection result state corresponds to the measured medication value being within a range approximating the expected medication value. The negative inspection result state corresponds to the measured medication value being outside a range approximating the expected medication value by a defined amount. The inconclusive inspection result state corresponds to comparison between the measured medication value and the expected medication value being inconclusive and is outside the range approximating the expected medical value, but not so much that it can be determined to be a negative inspection result.

At block 112, the second automated inspection is initiated by examining the different medications with a second measurement device that is associated with a second inspection property. A second measurement result is generated. By way of example and not of limitation, the second inspection process is a visual inspection process.

The illustrative method then proceeds to block 114 where the correct number of tablets is determined. The correct number of tablets is a quantitative measurement result.

At block 116, the illustrative method determines the color and shape of the tablets. The determination of color and shape is a qualitative measurement result.

A second inspection analysis is initiated at block 118. The second inspection analysis generates a second automated inspection result by comparing a second expected inspection value with the second measurement result as described above. A second measurement result is then generated. The method then proceeds to determine a second automated inspection result state by comparing a second expected inspection value with the second measurement result. Again, the second inspection result state includes a positive inspection result state, a negative inspection result state, and an inconclusive inspection result state, as described above.

Additional inspection steps may follow the second inspection as described herein. Thus, a third inspection as represented by inspection station 26 may follow. Furthermore, a fourth inspection such as final inspection 36 may also be performed. For example the fourth inspection, namely, final inspection station 36 may perform the scanning or identification of the bar codes for each preliminary package that is associated with the various labels and secondary container housing the preliminary packages.

At block 120, a multi-inspection analysis is performed by an analytical module 27. At a minimum, the analytical module 27 compares and then analyzes the first automated inspection result and the second automated inspection result for at least one package. Based on this analysis, the analytical module 27 selects one of a plurality of post-inspection states that are then communicated to the process control module. The post-inspection states include the manual inspection station state, the correction station state, and the assembly station state; each corresponding with the manual inspection station 30, correction station 32, and assembly station 34, respectively.

After the multi-inspection analysis, the selected post-inspection state is communicated to the process control module 24 that is communicatively coupled to the movement control module 28 that controls the conveyance of the preliminary package to the appropriate post-inspection station.

For example, the process control module 24 may receive an instruction that a particular preliminary package was improperly filled and that the preliminary package is to be transferred to the manual inspection station 30, then correction station 32, and finally to the assembly station 34.

In another example, the process control module 24 receives an instruction that the package was filled improperly and the package is transferred to the correction station 32 and then the assembly station 34.

In yet another example, the process control module 24 receives an instruction that the preliminary package was properly filled and the package is conveyed to the assembly station 34.

At block 122, the assembly station 34 begins the process of placing the preliminary packages in the illustrative box container. In the illustrative embodiment, the illustrative box container is configured to accommodate a 30-day supply of medication. The box container is also configured to receive a label that indicates the time of day or interval during which the medications within the pouch are to be consumed, e.g. morning, noon, evening, or bedtime. The illustrative box container is then glued or sealed.

The final package is then assembled at block 124. In the illustrative embodiment, the final package includes three boxes, in which each box is associated with a particular time of day. The illustrative time of day include morning, noon and evening. Additionally, the final package may include package inserts or a patient information sheet (PIS) and a detailed label that describes each of the medications.

The final package assembly may be performed by an automated means that reviews the prescription and labels, confirms that the appropriate inspections were performed for each preliminary package, confirms that the appropriate level of review by a pharmacist or technician has been performed, confirms that each container was sealed, and checks to see that the proper package insert was generated. By way of example and not of limitation, the package inserts have detailed information about indications, warnings, precautions, side effects, dosage, administration, and clinical pharmacology. The package inserts may also include summaries of the various medications being taken, and summaries of the side effects, and the associated administration. Although the package inserts are written primarily for a physician and pharmacist, the package inserts may be simplified so that they are easier for patients or caregivers to understand.

In certain instances, the final package may also include the PRN medications. PRN medications are consumed on an as-needed basis. Most often PRN medications are analgesics such as Tylenol®, laxatives, sleeping aids, and similar medications.

The final package may also require shipping labels or other such labels indicating that the final package is ready for pick-up. After the final package is validated, the final package is released and is ready for pick-up or shipping.

Figure 3:
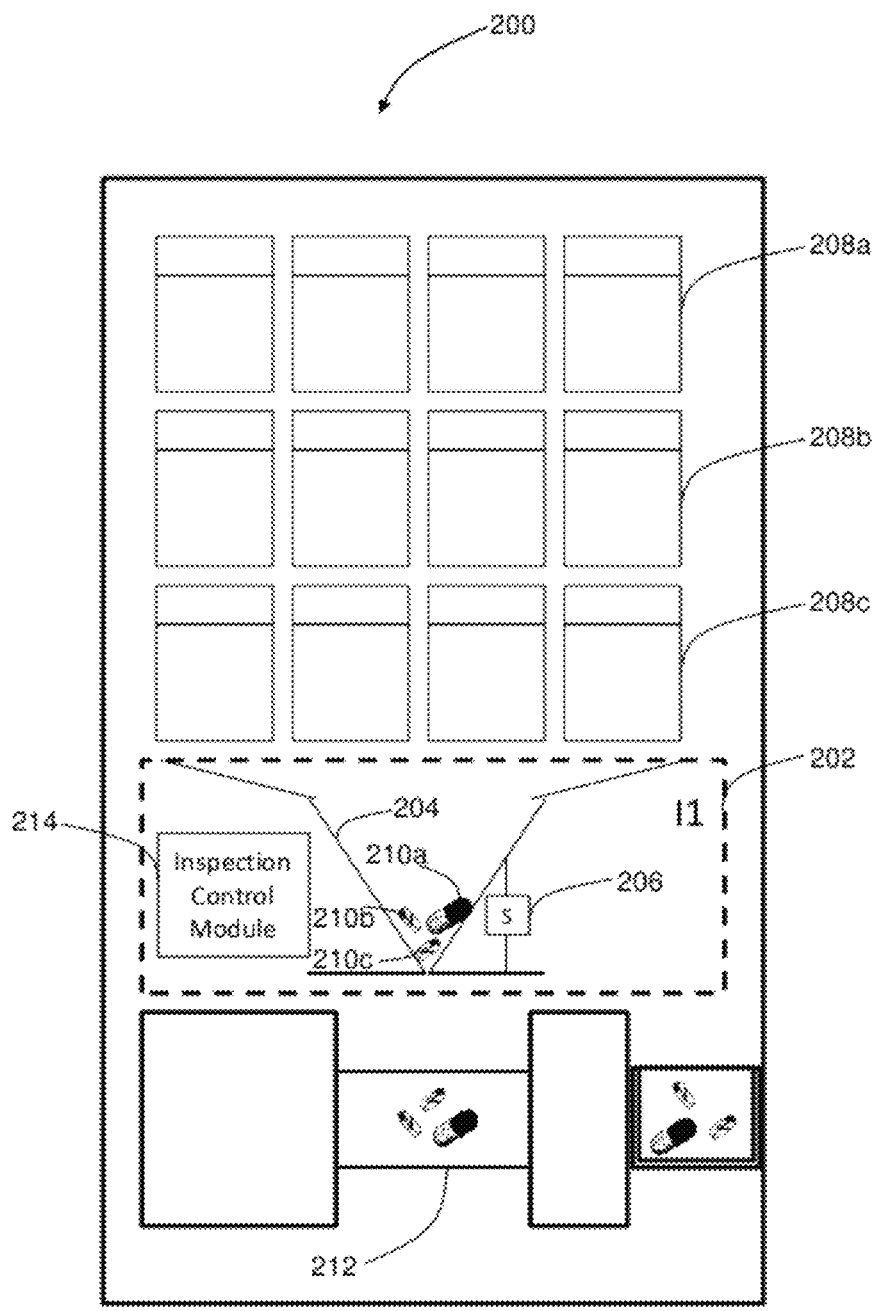
FIG. 3 shows an illustrative filling station that includes a first inspection station.

Referring to FIG. 3, there is shown an illustrative filling station 200 that includes a first inspection station 202. More particularly, the first inspection station 202 includes a hopper 204 and a precision weighing sensor 206, e.g. a scale. The hopper 204 captures the tablets released by re-fill modules 208. At the bottom of the hopper 204 is an electronically controlled a mechanism (not shown) that is configured to close the opening at the base of the hopper 204.

For example, re-fill modules 208a, 208b and 208c each release one tablet 210a, 210b, and 210c, respectively, that are captured by hopper 204 and then weighed by precision weighing device 206. When the tablets have settled in the hopper 204, the precision weighing sensor determines the weight of the hopper 204 and tablets 210. After subtracting the weight of the hopper 204 and associated components supported by the sensor 206, the weight of the tablets 210 is determined and communicated to inspection control module 214. After the weighing process has been completed, the hopper is opened and a preliminary packaging component 212 receives the tablets.

An illustrative filling station that may be retrofitted to support the systems and process described herein include the PARATA™ pharmacy automation station, also referred to as the PACMED™ station, in which the consumables sold by the McKesson Corporation. Other filling systems may also be used such as the YUYAMA™ filling technologies. Additionally, similar filling stations configured to provide an automated system for filling a preliminary package may be customized to support the systems and processes described herein.

In the illustrative embodiment of FIG. 3, the inspection station 202 is positioned before the preliminary packaging component 212 seals the pouches. Alternatively, the precision weighing inspection may be performed after the preliminary packaging component 212 seals the pouches.

In addition to automated filling, the filling system or filling station is configured to support generating a machine-readable representation of data for each preliminary package. By way of example and not of limitation, the machine-readable representation of data includes a barcode, matrix (2D) barcodes, radio frequency identification (RFID), or any combination thereof. Thus, the filling system 10 or filling station 200 is also configured to support generating a machine-readable representation that is associated with each preliminary package, which in turn is associated with a particular patient.

Analysis of the measured weight can be accomplished by the inspection control module 214. In one illustrative embodiment a database (not shown) has an entry for each tablet type indicating the nominal weight and the maximum normal variation. With this information, a table for the specific combination of tablets in a given container is constructed.

For example, a preliminary package receives three tablets, namely, tablets 210a, 210b and 210c, and the nominal weights are 100 milligrams, 150 milligrams and 200 milligrams, respectively. If each tablet has a 5% weight tolerance then the expected weight of the three tablets is estimated to range from 427.5-472.5 milligrams. This estimated range represents the expected medication value. In operation, the inspection control module 214 then compares the expected medication value to the measured medication value to generate the inspection result state as described above.

Figure 4A:
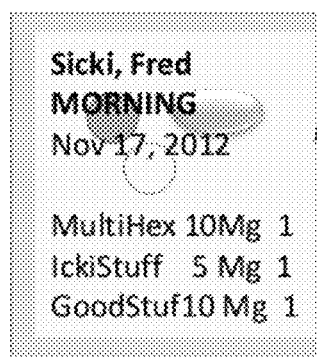
FIGS. 4A-4E show different preliminary packages and FIG. 4E shows a sleeve that receives the blister preliminary packages.

Referring to FIG. 4A there is shown a pouch 252 that holds multiple medications. The pouch is an illustrative preliminary package. As previously described, the pouch is heat sealed and is generally connected to other plastic pouches that contain similar medications.

Figure 4C:
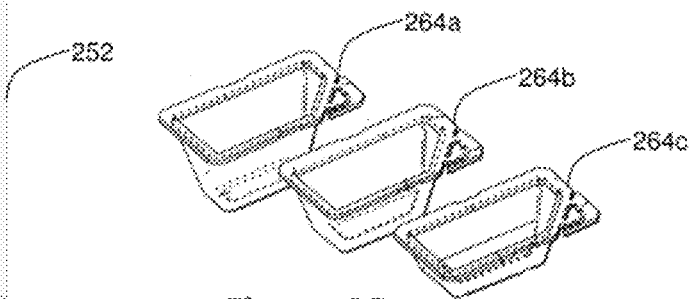
Figure 4B:
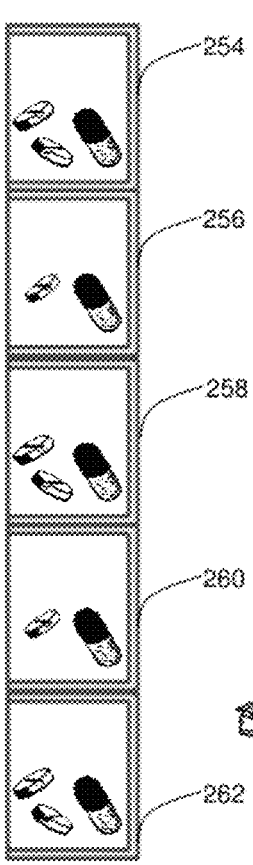

Referring to FIG. 4B there is shown five pouches that are connected to one another, wherein each pouch has different medications and the number of medications differs from pouch to pouch. More particularly, a first pouch 254 holds three tablets, the second pouch 256 holds two tablets, the third pouch 258 holds three tablets, the fourth pouch 260 holds two tablets, and the fifth pouch 262 holds three tablets.

Figure 4D:
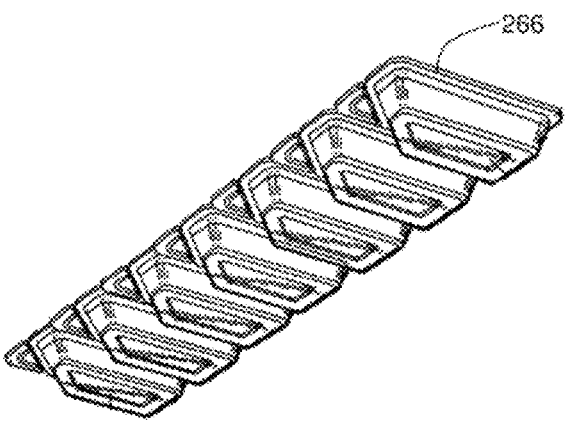
Figure 4E:
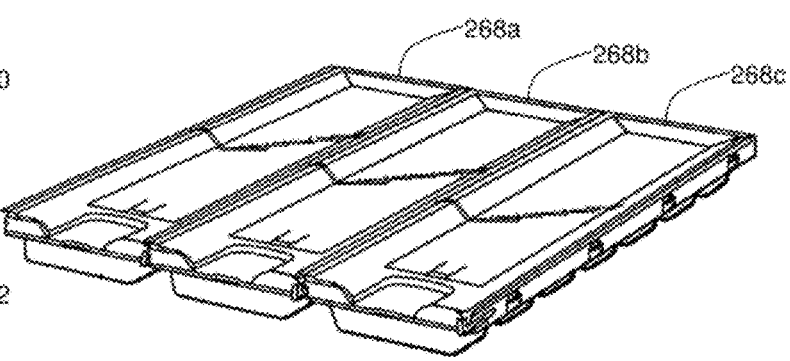

Referring to FIG. 4C there is shown a blister-type preliminary package 264a, 264b and 264c that are each of different size, i.e. height and volume. The blister is a formed plastic component that is configured to receive a removable cover. Each blister is configured to receive multiple medications and provides yet another illustrative embodiment of the preliminary package. Additionally, in FIG. 4D there is shown an isometric bottom view of a seven-day strip 266 of blisters that are adjacent to one another that are received by a sleeve (not shown). In FIG. 4E, illustrative sleeves 268a, 268b and 268c receive the blister preliminary packages are shown.

The preliminary package may be combined with the appropriate secondary containers or "final" package in a child-proof container or in a final package for the visually handicapped.

Figure 5A:
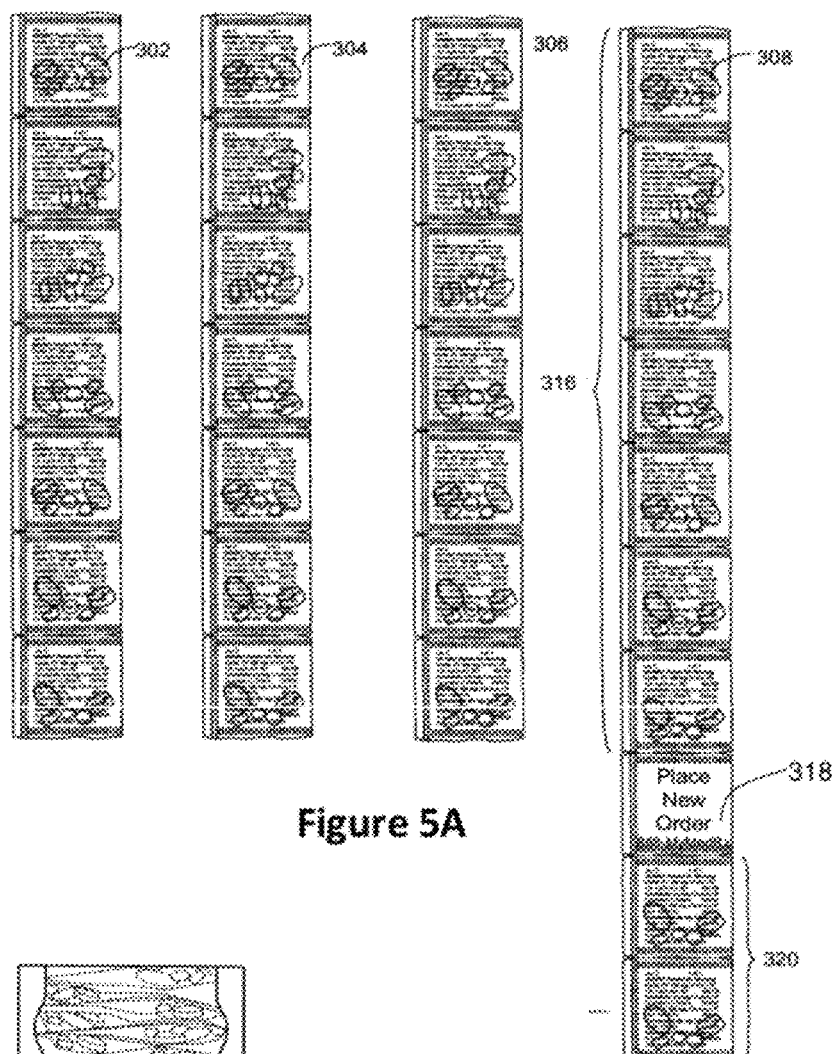
FIG. 5A shows separable sealed pouches in strips grouped together.

Referring to FIG. 5A, there is shown the separable sealed pouches that are grouped together. By way of example and not of limitation, there may be thirty pouches in a single collection that would be combined into the secondary box container shown in FIG. 5B. Alternatively, there may be a collection of seven pouches (for a seven-day box), twenty-eight pouches, or any grouping of pouches.

An illustrative 30-day grouping of sealed pouches may also be referred to as a strip, and the terms "strip" and "group of pouches" is used interchangeably in this patent application. The number of pouches in a strip may depend on the results of one or more inspections because one of the pouches may be found to be defective. Thus, when a defective pouch is identified, the defective pouch is removed and replaced at the correction station 32 (in FIG. 1), resulting in a separation of the previously connected 30-day grouping of sealed pouches.

In the illustrative embodiment, there are twenty-eight pouches followed by an empty pouch with printing on the pouch to remind the patient and/or caregiver to re-order, and two remaining pouches. Although shown as separate groupings, these separate pouches may be connected to one another and include a 30-day grouping of sealing pouches, in which the first seven-day group of pouches 302 is connected to the second seven-day-group of pouches 304 that, in turn, is connected to the third seven-day group of pouches 306, that is also connected to the fourth strip that includes a seven-day group of pouches 308, coupled to an empty pouch that is connected to the two remaining pouches 320.

The empty preliminary package 318 near the end of the sequence of preliminary packages may be empty and have markings that indicate to a patient or caregiver that the consumption of the medications in the preliminary packages is nearly exhausted. Additionally, this empty container can be used to print marketing and/or warning information in lieu of the normal patient information and or description of the medication contents. Examples of such messages might be: "PLEASE REORDER NOW", or "CALL 800-123-4567 TO REORDER NOW", or "CALL JOHN'S PHARMACY TO REORDER NOW".]

Figure 5B:
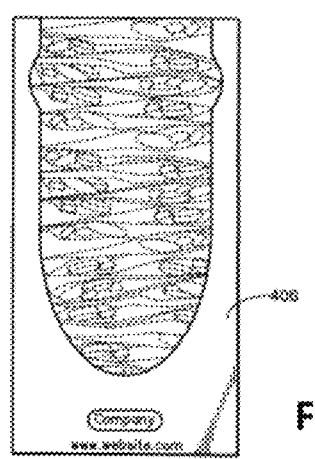
FIG. 5B shows the strips placed into a final box container package.

One or more strips are then placed in a final box container package as shown in FIG. 5B. The terms folded box, assembled box, and container box are used interchangeably to refer to the final package.

In the illustrative embodiment, the dosage period is selected from the group of dosage period intervals consisting of a morning dosage interval, a noon dosage interval, an evening dosage interval, or a bedtime dosage interval.

Figure 6:
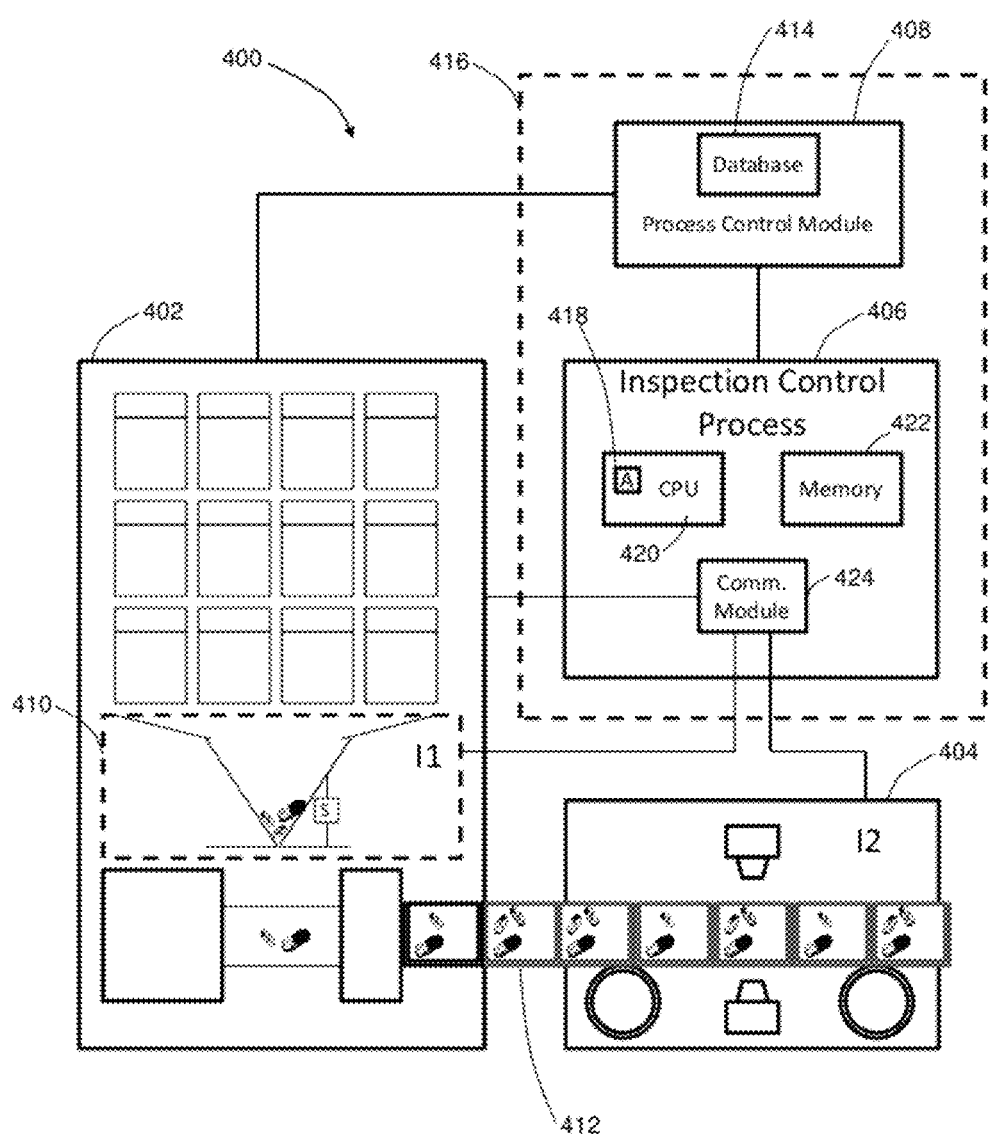
FIG. 6 shows a dual inspection station system.

Referring to FIG. 6 there is shown an illustrative dual inspection station system. The filling system 400 includes a filling station 402, a second inspection station 404, and a centralized inspection control process 406 that are each communicatively coupled to a process control module 408. The illustrative centralized inspection control process 406 receives raw sensor data from each inspection station and generates a measured medication value. The inspection control process 406 then compares the measured medication value to the expected medication value and generates an inspection result state.

The illustrative filling station 402 is communicatively coupled to the process control module 408 over a data communication network such as a local area network (LAN) using Ethernet and TCP/IP protocols. The process control module 408 is configured to provide real-time control and coordination of the various elements of the filling system 400 including, but not limited to, the filling station 402, the first inspection station 410, the conveyor 412, the second inspection station 404 and the inspection control process 406.

The illustrative filling station 402 passes control data to the process control module 408 and the centralized inspection control process 406. The process control module 408 identifies the medications that are placed into the preliminary packages that are subject to the multiple inspection processes described herein. The process control module 408 also selects each preliminary package that is inspected.

The illustrative filling station 402 communicates information that identifies the patient order associated with each preliminary package for such a patient order. The patient order may be received from a separate pharmacy management system (not shown) that generates an integrated order for processing as described above.

In the illustrative embodiment, the process control module 408 stores the integrated order information and accesses a medication database 414. The medication database 414 is a relational database management system that includes the expected inspection value for each inspection process that is associated with each medication. The illustrative database attributes include tablets weights and variances, color training data parameters, shape training parameters, tablet size data, tablet text information, qualitative values, quantitative values, and other such attributes that are capable of being stored in the medication database 414. Although, the database is presented as a sub-component of the process control module, the medication database 414 may be stored in the filling station 402, the pharmacy management system (not shown), or in any other memory module that is accessible to the illustrative process control module 408 via the illustrative LAN described herein.

In the illustrative embodiment, the process control module 408, the medication database 414, and the centralized inspection control process module 406 are disposed within stand-alone housing 416.

The centralized inspection control process 406 is communicatively coupled to both the first inspection station 410 and the second inspection station 404. The inspection control process receives raw inspection values from each medication value and generates a measured medication value. The "raw" values passed to the centralized inspection control process module 406 are then subjected to measurement techniques that analyze the signal/noise characteristics of the raw values, remove anomalies, filter the data, and perform other such analytical measurement techniques. As a result, the raw sensor data is converted to a measured medication value.

The inspection control process module 406 then compares the measured medication value to the expected medication value and generates an inspection result state.

An analytical module 418 associated with the inspection control process module 406 receives one or more inspection result states, analyzes the inspection result states, and selects a post-inspection state corresponding to one of a manual inspection station (not shown), a correction station (not shown), or an assembly station (not shown). The illustrative analytical module 418 is a software program that runs on a CPU 420 that is electrically coupled to memory 422. A communication module 424 enables the CPU to communicate instructions to the filling station 402, the first inspection station 410, the second inspection station 404, the conveyor 412, the process control module 408, and the database 414.

The illustrative analytical module 418 uses a decision table algorithm as shown in FIG. 10. For example, a manual inspection may only occur when there is a direct conflict between the results of inspection station #1 and inspection station #2, i.e. one positive inspection result and one negative inspection result. The decision table algorithm may be embodied in a control system, software, hardware, field programmable gate array, CPU, memory, and other such microprocessors and peripherals that are programmable, including a standard PC architecture or embedded equivalent. For illustrative purposes only, the sequential logic for the decision table algorithm of FIG. 10 is present in FIG. 11.

Figure 7:
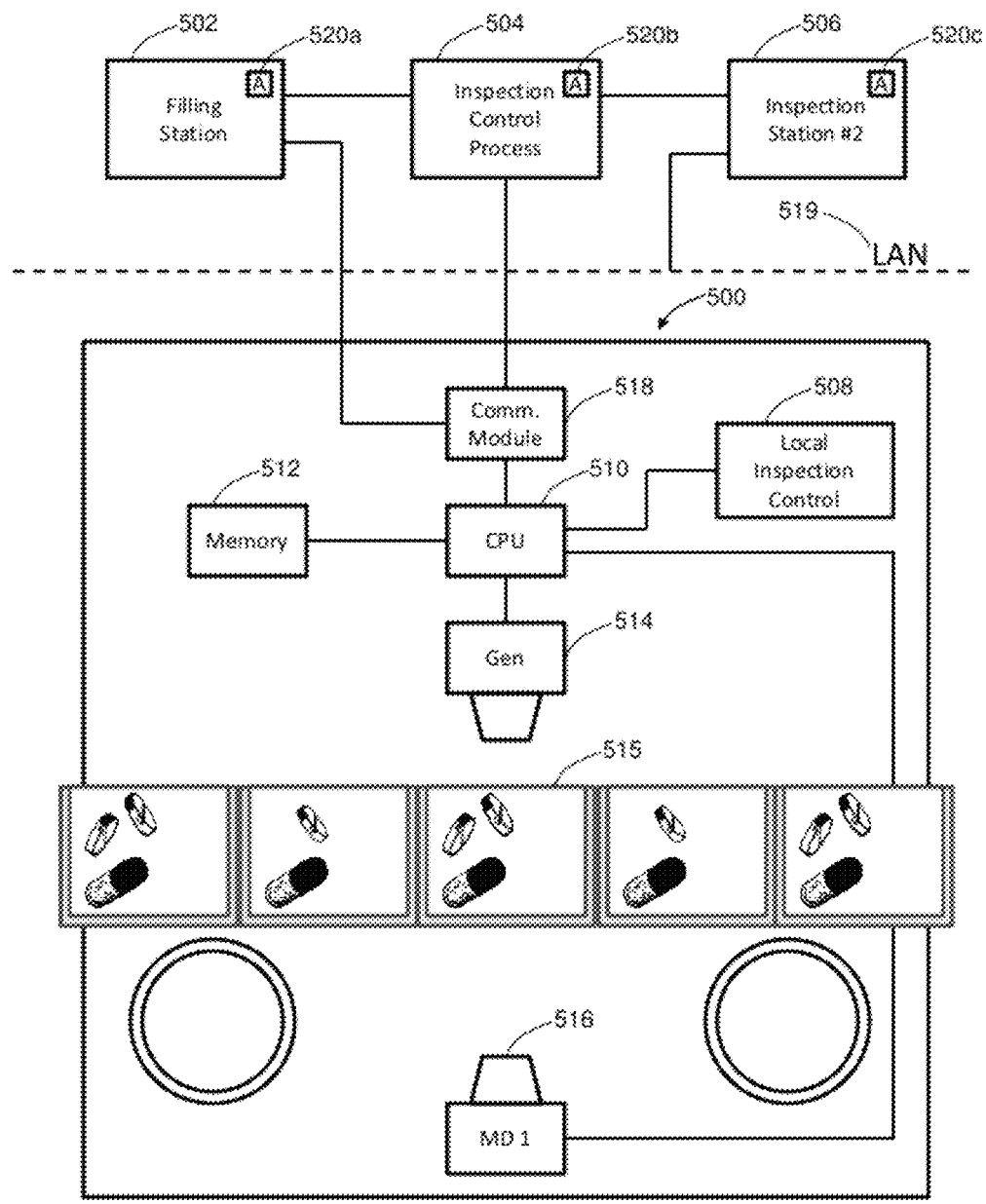
FIG. 7 shows an inspection station with local inspection control.

Referring to FIG. 7, there is shown an illustrative inspection station 500 with local inspection control. The inspection station 500 is communicatively coupled to filling station 502, inspection control process module 504, and another inspection station 506. The illustrative inspection station 500 includes a local inspection control module 508. In the illustrative embodiment, the local inspection control module 508 is a software module, in which instruction processing is performed by CPU 510 performing read/write operations in memory 512. The CPU is also communicatively coupled to a generator 514 and a measuring device 516. An illustrative generator 514 may include a diffuse visible light source, an X-ray generator source, or other such device that operates as an electromagnetic source, or sonic pressure wave source. The illustrative measuring device 516 provides a detection system that produces a raw detected value.

In operation, an illustrative pouch 515 is passed between the generator 514 and the measuring device 516. A raw value is collected by the measuring device 516 that is then communicated to the CPU 510. By way of example, the raw value is a raw visual image(s), raw X-ray images, tare weight, or any other such raw value that has not been subjected to the post-processing. The local inspection control module 508 performs the post-processing that generates a measured medication value. The measured medication value is then communicated via the communications module 518 and local area network (LAN) 519 to either the filling station 502, the inspection control process module 504, or to the other inspection station 506. An analytical module 520a, 520b, or 520c disposed in one of the filling station 502, inspection control process module 504, or next inspection station 506, respectively, performs the multi-inspection analysis as described herein.

Referring to FIG. 8, there is shown an illustrative embodiment of a stand-alone inspection control process system 550. The illustrative inspection control process system 550 includes a filling system 552 that communicates an expected measurement value 554 to an inspection control process module 556. The inspection control system 550 also includes an inspection station 558 that communicates an actual measurement value 560 to the inspection control process module 556. Additionally, more than one inspection station 562 can transmit actual measurement values 564 to the inspection control process module 556.

The inspection control process 556 includes logic embodied as hardware, software, or both, that performs a decision making process for each preliminary package. The illustrative decision making process is based on determining a likelihood that a preliminary package is filled correctly or incorrectly.

In operation, the inspection station 558 measures a physical property that corresponds to the preliminary package and communicates these actual measurements to the inspection control process module 556. The inspection control process module 556 also receives information from the illustrative filling system 552 that includes the expected measurements of the intended contents of each preliminary package that is subjected to an inspection. Alternatively, a database (not shown) may be accessed that includes a list of medications associated with the preliminary packages and the corresponding physical characteristics of each of these medications.

For example, the filling system 552 may pass data to the inspection control process module 556 that Tablet A and Tablet B are intended to be in the container under inspection. If the inspection process logic used the weighing of the tablets in the container, the inspection control process module 556 may access a database of all potential tablets that includes information that Tablet A has a weight between 200 and 210 milligrams, and Tablet B has a weight between 300 and 320 milligrams. The inspection control process module 556 determines the contents of the filled container have an expected measurement weight between 500 and 530 milligrams. The expected measurement weight and the actual measurement weight are analyzed by the inspection control process module 556 to determine whether the preliminary package has been properly filled.

In one embodiment, the inspection control process module 556 is a stand-along logic element.

In another embodiment, the inspection control process module may be integrated into another process within the system including, but not limited to, the filling system 552, the first inspection station 558, another inspection station 562, or any other system, module, or component that is communicatively coupled to the inspection control process module 556. For example, the expected measurement weight 554 could be transmitted from the control process 556 or filling system 552 directly to the inspection station 558. The inspection station 558 could then return a simple value to the control process module 556 indicating that the actual weight is consistent with the expected weight, or the actual weight is not consistent with the expected weight.

Inspection accuracy is improved with additional inspection stations. And the inspection control process module 556 may include the analytical module that performs the multi-inspection analysis. Multiple inspections improve the accuracy of inspection process. For example, although the weight of the medications may be accurate, one of the tablets may be broken in two or one of the tablets may have been accidentally replaced with a different tablet of the same or similar weight. A second inspection process that uses a different inspection process, e.g. visual inspection with visible light, can be used to supplement the findings from the first inspection station. Thus, an optical inspection process may be capable of counting the tablets in the preliminary package, or determine the color and shape of the tablets. An error in the tablet count (as in the case of the broken tablet) enables the control process module 556 to identify the preliminary package as being improperly filled. Other inspection processes as described herein may also be used.

In addition to identifying improperly filled preliminary packages, the inspection control process module 556 also has the capability of marking an improperly filled preliminary package. In one embodiment, the filling process is stopped until a corrective action is taken by a human. In another embodiment, the inspection control process module 556 may physically mark an improperly filled or suspect container. If the filling system is sufficiently automated and includes a conveyor system, the inspection control process 556 may pass information to the process movement control module 566 that the improperly filled preliminary package and those preliminary packages associated with the same integrated order are to be routed to a correction station before final order assembly.

Furthermore, the illustrative inspection control process module 556 is also communicatively coupled to a personal computer 568 that is accessible by correction and assembly personnel. The personal computer 568 displays the results of all inspections and analysis available to a technician. The inspection control process module 556 generates a record of all the inspection results and analysis associated with each patient order. The records can be used for data inquiry or to generate more detailed historical reports.

The illustrative movement control process 566 may be embodied as a software process in a standard PC with UNIX or Microsoft Windows as an operating system. The movement control process 566 may have access to a Microsoft SQLServer database with records for each potential tablet type, and associate physical properties with each tablet that are appropriate to the type of inspection devices that are implemented in the system. Communication of information between the various processes could be accomplished with any of a variety of messaging mechanisms provided in various operating system environments. A separate utility program would be used to maintain that database and update it periodically as tablets are removed or new tablet types are introduced or new generic versions of tablets are added to the system.

Referring to FIG. 9A-9C there is shown an illustrative inspection and multi-inspection method that inspects preliminary packages that include one or more different medications. The method is initiated at block 602 wherein inspection parameters are selected by one of the inspection control modules or inspection stations described above.

The method then proceeds to block 604 where tablets are identified for inspection. The tablets are selected by an automated filling system that receives a verified and integrated patient order. A preliminary package is filled with the multiple medications that generally include tablets.

As described above, each inspection station receives at least two medications in at least one preliminary package. At block 606, the expected tablet values for each inspection parameter are received by the either the inspection station or the inspection control process module.

In the illustrative embodiment, the expected tablet data for each preliminary package are communicated to the inspection control process in block 608. As previously described, the expected tablet data corresponds to one or more inspection parameters. The method then proceeds to block 610 where the measurement data from an inspection station is received. As previously described, the inspection station includes a measurement device that corresponds to the inspection station.

At block 610, the illustrative inspection control process module obtains the measurement device data from each inspection station and a first inspection analysis is completed by the analytical module at block 612. The method then proceeds to block 614, in which a comparison is initiated between the measurement data and the expected values of the first inspection station. Based on this comparison, the illustrative inspection control process or inspection station then proceeds to select an inspection result state. The inspection result state includes a positive inspection result state, a negative inspection result state, and an inconclusive inspection result state.

At decision diamond 616, a determination is made to perform a multi-inspection analysis. A multi-inspection analysis may not be necessary and so the multi-inspection process can be bypassed to expedite the processing and handling of the patient order. For example, a single tablet may be carried in a particular preliminary package or single type of tablet may be placed in a particular pouch. As a result, a single inspection process may be satisfactory such as the precision weighing process described above.

When a preliminary package having multiple different medications is received, a decision to proceed with a multiple inspection process is made at decision diamond 616. At block 618, the second inspection analysis is performed. The illustrative second inspection is an optical inspection that analyzes the size, shape, and color of each tablet. At block 620, an inspection step compares the measurement data from the second inspection station to the expected values that corresponds the second inspection station.

The determination to perform another inspection is made at decision diamond 622. If the decision is to perform another inspection, the method proceeds to the next inspection station. By way of example, the third inspection may be an X-ray inspection process.

If the inspection steps for the selected preliminary package have been completed, the method proceeds to block 624 where a multiple inspection analysis is performed. After the multiple inspection analysis is completed, a determination is made to proceed to the manual inspection station at decision diamond 626. If a manual inspection is necessary, the preliminary package is sent to manual inspection station at block 628.

If the manual inspection is not required, the method then proceeds to determine whether a correction step is necessary as shown in decision diamond 630. If a correction step is needed, the method proceeds to correction station block 632 where the preliminary package is conveyed to the correction station. At block 634, the method then proceeds to the assembly station as described above.

Referring now to FIG. 10, there is shown an illustrative decision table 700 for the multi-inspection analysis of two inspection stations. In column 702, the inspection result states of the first inspection station are presented wherein "good" refers to a positive inspection result state, "bad" refers to a negative inspection result state, and "inconclusive" refers to an inconclusive result state. Each of the inspection result states are described above in further detail. In column 704, the inspection result states for the second inspection station are presented.

The multi-inspection analysis is then performed. In column 706, the decision to convey packages to manual inspection is based on analyzing the inspection results in columns 702 and 704. The decision to convey a package to the correction station in column 708 is also based on analyzed the combined inspection results. An illustrative sequential flowchart 710 of the decision table 700 that may be programmed for a logic controller is shown in FIG. 11.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. An inspection system that inspects at least two different medications, the inspection system comprising:
    an automated filling station that has a supply of at least two different medications, which are received by a plurality of packages;
    an automated inspection station that receives the at least two different medications;
    a plurality of measurement devices, wherein each measurement device is configured to examine the different medications and generate a measured medication value for the different medications;
    an inspection control process module communicatively coupled to the automated filling station and the automated inspection station, wherein a plurality of measured medication values generated by the plurality of measurement devices are received by the inspection control process module;

an expected medication value received by the inspection control process module; and an inspection result state selected by the inspection control process module, when the inspection control module compares the expected medication value to the measured medication values, wherein the inspection result state includes a positive inspection result state, a negative inspection result state, and an inconclusive inspection result state.

2. The inspection system of claim 1, wherein at least one measurement device examines the different medications before the automated filling station fills each package with the different medications.

3. The inspection system of claim 1, wherein at least one measurement device examines the different medications after the automated filling station fills each package with the different medications.

4. The inspection system of claim 1 further comprises two measurement devices, in which a first measurement device examines the different medications before the automated filling station fills each package with the different medications, and a second measurement device examines the different medications after the automated filling station fills each package with different medications.

5. The inspection system of claim 1, wherein the automated filling station houses the automated inspection station, the measurement device, and the inspection control process module.

6. The inspection system of claim 1 further comprising a stand-alone inspection station housing that is communicatively coupled to the automated filling station, the stand-alone inspection station housing including the automated inspection station, the measurement device and the inspection control process module.

7. The inspection system of claim 1 further comprising a stand-alone inspection control process module that is communicatively coupled to the inspection station and the automated filling station, wherein the measurement device is housed by the automated inspection station.

8. The inspection system of claim 1 further comprising a process control module communicatively coupled to the automated filling station, the automated inspection station and the inspection control module, the process control module configured to convey the medications according to the inspection result state.

9. The inspection system of claim 1 further comprising a second inspection system that generates a second inspection result state, in which the inspection result state and the second inspection result state are analyzed by an analytical module.

10. The inspection system of claim 1 wherein the measurement device is selected from the group consisting of a camera, a video, a precision weighing component, and an X-ray.

11. An inspection system that inspects at least two different medications, the inspection system comprising:

an automated filling system that houses at least two different medications, which are received by a plurality of packages;

an automated inspection system that receives the plurality of medications associated with at least one of the packages;

at least two measurement modules, in which each measurement module is configured to examine the different medications and generate a measured medication value for the different medications;

an inspection control process module communicatively coupled to the automated filling system and the automated inspection system, wherein a plurality of measured medication values generated by the plurality of measurement modules are value is received by the inspection control process module;

an expected medication value received by the inspection control process module; and an inspection result state selected by the inspection control process module, when the inspection control module compares the expected medication value to the measured medication values, wherein the inspection result state includes, a positive inspection result state corresponding to the measured medication value being in a range approximating the expected medication value, a negative inspection result state corresponding to the measured medication value being outside a range approximating the expected medication value, and an inconclusive inspection result state corresponding to comparison between the measured medication value and the expected medication value being inconclusive.

12. The inspection system of claim 11, wherein at least one measurement module examines the different medications before the automated filling system fills each package with the different medications.

13. The inspection system of claim 11, wherein at least one measurement module examines the different medications after the automated filling system fills each package with the different medications.

14. The inspection system of claim 11 that includes a first measurement module that examines the different medications before the automated filling system fills each package with the different medications, and a second measurement module that examines the different medications after the automated filling system fills each package with different medications.

15. The inspection system of claim 11, wherein the automated filling system houses the automated inspection system, the measurement modules and the inspection control process module.

16. The inspection system of claim 11 further comprising a stand-alone inspection housing that is communicatively coupled to the automated filling system, the stand-alone inspection housing including the automated inspection system, the measurement modules and the inspection control process module.

17. The inspection system of claim 11 further comprising a stand-alone inspection control process module that is communicatively coupled to the inspection system and the automated filling system, wherein the measurement modules are housed by the automated inspection system.

18. The inspection system of claim 11 further comprising a process control module communicatively coupled to the automated filling system, the automated inspection system and the inspection control module, the process control module configured to convey the medications according to the inspection result state.

19. The inspection system of claim 11 further comprising a second inspection system that generates a second inspection result state, in which the inspection result state and the second inspection result state are analyzed by an analytical module.

20. The inspection system of claim 11 wherein the measurement device is selected from the group consisting of a camera, a video, a precision weighing component, and an X-ray.

21. An inspection method that inspects at least two different medications, the method comprising:
- housing at least two different medications in a plurality of packages, wherein the medications and the packages are filled by an automated filling system;
- enabling an automated inspection system to receive the plurality of medications associated with at least one of the packages;
- examining the different medications with at least two measurement modules, in which each measurement module is configured to examine the different medications and generate a measure medication value for the different medications;
- communicatively coupling an inspection control process module with the automated filling system and the automated inspection system, wherein a plurality of measured medication values generated by the plurality of measurement devices is received by the inspection control process module;
- communicating an expected medication value to the inspection control process module; and
- enabling the inspection control process module to select an inspection result state, when the inspection control module compares the expected medication value to the measured medication values, wherein the inspection result state includes a positive inspection result state, a negative inspection result state, and an inconclusive inspection result state.

22. The inspection method of claim 21, wherein at least one measurement module examines the different medications before the automated filling system fills each package with the different medications.

23. The inspection method of claim 21, wherein at least one measurement module examines the different medications after the automated filling system fills each package with the different medications.

24. The inspection method of claim 21 that includes a first measurement module to examine the different medications before the automated filling system fills each package with the different medications, and enabling a second measurement module to examine the different medications after the automated filling system fills each package with different medications.

25. The inspection method of claim 21, wherein the automated filling system houses the automated inspection system, the measurement modules and the inspection control process module.

26. The inspection method of claim 21 further comprising enabling a stand-alone inspection housing to communicate with the automated filling system, wherein the stand-alone inspection housing includes the automated inspection system, the measurement modules and the inspection control process module.

27. The inspection method of claim 21 further comprising enabling a stand-alone inspection control process module to be communicatively coupled to the inspection system and the automated filling system, wherein the measurement modules are housed by the automated inspection system.

28. The inspection method of claim 21 further comprising enabling a process control module to be communicatively coupled to the automated filling system, the automated inspection system and the inspection control module, the process control module configured to convey the medications according to the inspection result state.

29. The inspection method of claim 21 further comprising a second inspection system that generates a second inspection result state, in which the inspection result state and the second inspection result state are analyzed by an analytical module.

30. The inspection method of claim 21 wherein the measurement device is selected from the group consisting of a camera, a video, a precision weighing component, and an X-ray.

* * * * *